United States Patent
Denomme et al.

(10) Patent No.: US 11,927,530 B2
(45) Date of Patent: Mar. 12, 2024

(54) PLASMON RESONANCE SYSTEM, INSTRUMENT, AND DEVICE FOR MEASURING MOLECULAR INTERACTIONS

(71) Applicant: Nicoya Lifesciences, Inc., Kitchener (CA)

(72) Inventors: Ryan Denomme, Kitchener (CA); Shawn Fitzpatrick, New Hamburg (CA); Jason Garr, Hamilton (CA); Krishna Iyer, Waterloo (CA); Gordon Hall, Milton (CA); Champika Samarasekera, Guelph (CA)

(73) Assignee: Nicoya Lifesciences Inc., Kitchener (CA)

( * ) Notice: Subject to any disclaimer, the term of this patent is extended or adjusted under 35 U.S.C. 154(b) by 236 days.

(21) Appl. No.: 17/278,450

(22) PCT Filed: Sep. 30, 2019

(86) PCT No.: PCT/CA2019/051396
§ 371 (c)(1),
(2) Date: Mar. 22, 2021

(87) PCT Pub. No.: WO2020/061715
PCT Pub. Date: Apr. 2, 2020

(65) Prior Publication Data
US 2022/0003673 A1 Jan. 6, 2022

Related U.S. Application Data

(60) Provisional application No. 62/738,795, filed on Sep. 28, 2018.

(51) Int. Cl.
*G01N 21/552* (2014.01)
*G01N 21/05* (2006.01)

(52) U.S. Cl.
CPC .......... *G01N 21/553* (2013.01); *G01N 21/05* (2013.01); *G01N 2201/0438* (2013.01); *G01N 2201/062* (2013.01)

(58) Field of Classification Search
CPC ..... B01L 2300/0816; B01L 2300/0877; B01L 2300/1822; B01L 2400/0633;
(Continued)

(56) References Cited

U.S. PATENT DOCUMENTS

| | | | |
|---|---|---|---|
| 6,887,713 | B2 | 5/2005 | Nelson et al. |
| 7,724,373 | B2 | 5/2010 | Glazier et al. |

(Continued)

FOREIGN PATENT DOCUMENTS

| | | |
|---|---|---|
| CA | 2328599 A1 | 11/1999 |
| CA | 2750900 A1 | 8/2010 |

(Continued)

OTHER PUBLICATIONS

Jonsson et al. Real-time biospecific interaction analysis using surface plasmon resonance and a sensor chip technology. Biotechniques 11:620-627 (1991).

(Continued)

*Primary Examiner* — Sunghee Y Gray

(57) ABSTRACT

A plasmon resonance (PR) system, instrument, and/or device and configurations thereof for measuring molecular interactions is disclosed. In some embodiments, the PR system, instrument, and/or device is a localized surface plasmon resonance (LSPR) system, instrument, and/or device. In other embodiments, the PR system, instrument, and/or device is a surface plasmon resonance (SPR) system, instrument. The PR system, instrument, and/or device may include, for example, force feedback for reliable flow cell sealing, optical feedback for reliable flow cell sealing, local thermal control of an LSPR chip (e.g., a ring Peltier, a (Continued)

continuous Peltier), dual displacement pumps for constant flow delivery to a microfluidic device, a dual channel LSPR sensor, and any combinations thereof.

18 Claims, 23 Drawing Sheets

(58) Field of Classification Search
CPC ....... B01L 3/502715; B01L 7/00; G01N 1/38; G01N 2021/135; G01N 21/05; G01N 21/11; G01N 21/13; G01N 21/553; G01N 21/554; G01N 21/648; G01N 2201/024; G01N 2201/0438; G01N 2201/062; G01N 33/54373
USPC .......................................................... 356/445
See application file for complete search history.

(56) References Cited

U.S. PATENT DOCUMENTS

| | | | |
|---|---|---|---|
| 8,693,003 B2 | 4/2014 | Nieva et al. | |
| 9,322,823 B2 | 4/2016 | Denomme et al. | |
| 9,958,438 B2 | 5/2018 | Sjolander | |
| 10,794,904 B2 | 10/2020 | Denomme et al. | |
| 11,278,890 B2 | 3/2022 | Denomme et al. | |
| 11,598,771 B2 | 3/2023 | Denomme et al. | |
| D983,682 S | 4/2023 | Lubjenka et al. | |
| 2003/0022388 A1 | 1/2003 | Roos et al. | |
| 2006/0109472 A1 | 5/2006 | Muraishi | |
| 2006/0203237 A1* | 9/2006 | Ji | G01N 21/0303 356/246 |
| 2009/0263285 A1 | 10/2009 | Malmqvist et al. | |
| 2011/0316522 A1* | 12/2011 | Shinobu | G01N 5/02 324/109 |
| 2013/0295587 A1 | 11/2013 | Sjobom | |
| 2014/0219871 A1* | 8/2014 | Sjolander | G01N 33/54366 422/69 |

FOREIGN PATENT DOCUMENTS

| | | |
|---|---|---|
| CA | 2808412 A1 | 2/2012 |
| CA | 2846909 A1 | 9/2014 |
| CA | 3061157 A1 | 3/2020 |
| EM | 0080464110001 | 10/2020 |

OTHER PUBLICATIONS

PCT/CA2019/051396 International Search Report and Written Opinion dated Dec. 10, 2019.

Zhang et al., Optical biosensor for sensitive and fast detection of ampicillin residues in milk samples. 2009 Symposium on Photonics and Optoelectronics. pp. 1-4, (2009). doi:10.1109/SOPO.2009.5230148.

* cited by examiner

OpenSPR™ 2 Channel Instrument for Protein Interaction Analysis

Summary

- In this application note, we demonstrate how OpenSPR's 2 channel operation can be used to improve kinetic analysis of protein interactions
- A 1:1 kinetic interaction model was used to determine the kinetics of the interaction between Protein A and Human IgG
- The affinity constant of the interaction was determined to be 0.76 nM
- OpenSPR™ provides an affordable benchtop solution for kinetic analysis of protein interactions and many other important applications.

Overview

OpenSPR™ is a powerful instrument providing in-depth label-free binding kinetics for a variety of different molecular interactions. The determination of kinetic binding constants for antibody-antigen interactions is critical in many research and development applications. These are often high-affinity interactions which can make them challenging for analysis.

A well-known example of a high affinity interaction is that between Protein A and Human IgG. Protein A is commonly used as a capture molecule for IgG antibody immobilization, providing strong and reliable capture with a low dissociation rate. In this application note, OpenSPR™ is used to measure the affinity and kinetics between Protein A and Human IgG. We demonstrate how the 2-channel OpenSPR is able to quickly and easily generate high quality data by simultaneously removing any drift and/or non-specific binding via the reference channel.

Materials and Equipment

- OpenSPR™ 2 Channel Instrument
- OpenSPR Carboxyl Sensor Chip and Amine Coupling Kit
- TraceDrawer™ Kinetic Analysis Software
- Ligand: Protein A
- Analyte: Human IgG
- Running Buffer: HBS-EP, pH 7.4
- Regeneration solution: 10 mM Glycine-HCl, pH 2.5

Procedure

1. Perform the OpenSPR instrument setup procedure following the software guides.
2. Load the Carboxyl Sensor into the OpenSPR instrument.
3. Run the Ligand Wizard to immobilize 20 μg/ml of Protein A onto Channel 2 of the Carboxyl sensor chip. Channel 1 is activated and blocked and serves as the reference.
4. Prepare 150 μL Human IgG analyte dilutions into the Running Buffer at the following concentrations: 111 nM, 37 nM, 12.1 nM, and 4.1 nM.
5. Inject the analyte solutions individually at a flow rate of 40 μL/min with an association time of 120 s and a dissociation time of 600 s.
6. Between each analyte measurement, perform an injection of the Regeneration Solution (10 mM glycine-HCl, pH 2.5) at a flow rate of 150 μL/min. This will remove the bound analyte and regenerate the Protein A ligand surface.
7. Finish the test and import the processed data into the TraceDrawer analysis software. Calculate the binding kinetics with a 1:1 binding model.

*FIG. 18A*

PLASMON RESONANCE SYSTEM, INSTRUMENT, AND DEVICE FOR MEASURING MOLECULAR INTERACTIONS

RELATED APPLICATIONS

This application is a U.S. National Stage Application of PCT/CA2019/051396 filed on Sep. 30, 2019, which claims the benefit of U.S. Provisional Application No. 62/738,795 filed on Sep. 28, 2018, the entirety of which is incorporated herein by reference.

TECHNICAL FIELD

The presently disclosed subject matter relates generally to the detection of molecules, such as DNA, proteins, and the like, and more particularly to the analysis of analytes using a plasmon resonance (PR) system, instrument, and/or device and configurations thereof for measuring molecular interactions.

BACKGROUND

In traditional assays, the protein or DNA arrays are flooded with a solution containing labeled target biomolecules, incubated overnight, rinsed, and then "read-out" using fluorescence detection methods. This is not only time-consuming but requires large sample concentrations. Direct, label-free detection techniques exist, such as surface plasmon resonance (SPR). However, these techniques exhibit lower sensitivity and throughput, thus making them unsuitable for detection of very low concentrations of the target analyte. SPR technology has certain shortcomings. For example, immunoassays using SPR technology can be expensive, may require complex microfluidics systems and high precision optics, may require complex assays, is a niche technology with few specialists, lack intelligence, and so on.

SUMMARY

Accordingly, the invention includes embodiments of a plasmon resonance (PR) system, instrument, and/or device that may include features that facilitate benefits in relation to performing SPR analysis using the PR system, instrument, and/or device. For example, embodiments described herein may facilitate improved approaches to providing sealing between a flow cell and a sensor chip in a PR system. Furthermore, embodiments described herein may facilitate thermal control over a sensor chip during performance of SPR analysis. Also, improvements in the fluidic delivery system for providing fluid to a flow cell of a PR system are also described. Further still, improved flow cells are discussed that may provide flexibility and/or additional features to be provided in SPR analysis. In addition, a conveniently interchangeable light source is contemplated for use in a SPR analysis.

The invention may include embodiments directed to a PR system, instrument, and/or device that includes relative movement between a flow cell and a sensor chip to provide fluidically sealed engagement between the flow cell and the sensor chip. This may include inducing relative movement between the flow cell and the sensor chip to achieve sealing between the flow cell and the sensor chip. For example, a linear actuator may be provided that moves the sensor chip into sealing engagement with the flow cell. As may be appreciated, sufficient force application may be required to facilitate sealing engagement between the flow cell and the sensor chip; however, excess force may result in the fluidic channel of the flow cell collapsing, sensor damage, flow cell damage, or other disadvantages. Accordingly, embodiments are provided herein that facilitate means for accurately determining adequate force application between the flow cell and the sensor chip. One approach includes utilization of force feedback on the linear actuator that produces the movement between the flow cell and the sensor chip. Another approach may include monitoring of optical properties to determine when the flow cell and sensor chip are sufficiently engaged to provide sealing engagement, without excess force being applied.

Furthermore, various approaches to providing thermal control of the sensor chip in a PR system, instrument and/or device are contemplated herein. Use of a thermal control device such as a thermoelectric device is contemplated. Preferably, the thermal control device may be disposed in close proximity to the sensor chip to provide increased thermal control and thermal efficiency. However, for the PR system to operate in transmission mode, the thermal control device may be positioned outside of the optical path. Accordingly, in one embodiment described herein, a thermal control device is disposed in contacting engagement with the sensor chip yet is shaped to be located outside of the optical path. One approach may include providing a ring-shaped Peltier device in contact with the sensor chip and disposed such that an aperture of the ring-shaped Peltier device facilitates an unobstructed optical path relative to the sensor chip. Alternative approaches are also described in which a thermal control device may be disposed adjacent to a sensor chip holder and outside the optical path for providing thermal control of the sensor chip holder, and in turn the sensor chip retained therein.

Furthermore, the fluidic characteristics of a PR system, instrument, and/or device may be advantageously facilitated by using a plurality of pumps for provision of fluid to the flow cell of the PR system, instrument, and/or device. It is presently recognized that displacement pumps may be relatively well suited for use in the context of a PR system. However, such pumps may have certain drawbacks such as volumetric capacity limitations. Furthermore, upon initial operation, such pumps may experience transient operations as the pump comes to speed and achieves steady-state operation to provide a constant flow rate with low noise.

Accordingly, the invention includes an embodiment that utilizes a plurality of pumps for provision of fluid to the flow cell of the PR system, instrument, and/or device. In the embodiments described herein, a first pump may be primed and initially operated with the first pump outputting fluid to a waste port to allow the first pump to achieve steady-state operation (e.g., for the motor powering the first pump to achieve steady-state speed). In turn, the first pump may be directed to provide flow to the SPR sensor once it has achieved steady-state operation. While the first pump is providing flow to the SPR sensor, a second pump may also be primed and initially operated with the second pump connected to a waste port to allow the second pump to achieve steady-state operation. Once the second pump has achieved steady-state operation and the first pump has expended its volumetric capacity, the supply to the SPR sensor may be switched from the first pump to the second pump. Thereafter, the first pump may be primed and connected to a waste port to allow for operation of the first pump to achieve steady-state operation. In turn, the provision of fluid to the SPR sensor may be again provided to the first pump once the second pump has expended its volumetric capacity. Accordingly, operation of the plurality of pumps may be interleaved such that a pump may be primed and purged to waste prior to achieving steady-state operation while another of the pumps provides fluid flow to the SPR sensor. In this regard, constant flow with low noise may be achieved for fluidic volumes greater than that capable of being achieved with a single pump. Furthermore, approaches to operation of the plurality of pumps are described it may provide advantages in relation to fluid switchover such as for modifying the buffer solution or other fluid in the fluidic system.

Furthermore, embodiments of the flow cell are described herein that may allow for a plurality of channels to be defined relative to an SPR sensor. This may facilitate a dual channel SPR sensor that provides highly consistent sensor properties. Accordingly, a reference sensor may be provided, or a plurality of analyte detection channels may be provided for concurrent analysis.

Further embodiments presented herein include an interchangeable light source that may provide efficient modification or interchange of light sources for use in various sensing approaches. For instance, a plug-in socket style connector may be provided for receipt of a light source (e.g., on a circuit board or the like). In this regard, the light source may be efficiently interchanged by exchanging the board on which the light source is provided.

Accordingly, the embodiments described herein may facilitate advantages to a PR system, instrument and/or device as will be appreciated the discussion to follow.

In accordance with an aspect of the present invention, a plasmon resonance system for measuring properties of molecular interactions may include a sensor chip, a flow cell, and an actuator. The sensor chip may include a detection region. The flow cell may include a fluid channel for circulating fluid across the detection region of the sensor chip. The actuator may be configured to control relative movement of the sensor chip with respect to the flow cell between an undocked configuration in which the sensor chip is spaced apart from the flow cell and a docked configuration in which the sensor chip is in contact with the flow cell to seal a volume of space between the sensor chip and the flow cell. In some arrangements, the actuator may be an electrically-driven linear actuator.

The system may further include a shuttle supporting either the sensor chip or the flow cell. The shuttle may be in operative engagement with the actuator for linear movement of the sensor chip or the flow cell with respect to the other. The system may also include a pedestal which remains stationary and supports whichever of the sensor chip or the flow cell is not supported by the shuttle.

In some embodiments, the sensor chip may be constructed of either glass or plastic and the flow cell may be constructed of either polydimethylsiloxane or a fluoroelastomer. However, it is contemplated that any suitable materials may be used for construction of the sensor chip and/or the flow cell.

The plasmon resonance system may further include a load sensor configured to determine a force between the sensor chip and the flow cell resulting from movement of the linear actuator. A controller may be configured to receive a signal from the load sensor, the signal being indicative of a magnitude of the force. The controller may further be configured to cease movement of the linear actuator in response to the magnitude of the force exceeding a threshold value. The threshold value may correspond to a force associated with the docked configuration. In this regard, the actuator may move the component supported by the shuttle (e.g., either the flow cell or the sensor chip) toward the component supported by the pedestal until the load sensor indicates a desired force between the flow cell holder and sensor chip holder has been reached.

In some embodiments, the system may further include an optical system configured to determine a displacement of a portion of the flow cell occurring in response to a force between the sensor chip and the flow cell resulting from movement of the linear actuator. The portion of the flow cell may be an elastically deformable channel configured to collapse in response to a collapse force from the linear actuator. For example, the elastically deformable channel may be a portion of the fluid channel. Moreover, the linear actuator may be configured to retract a preset distance in response to the optical system determining the elastically deformable channel has collapsed.

Alternatively, the portion of the flow cell may include a plurality of measurement indentations, each configured to collapse under a different predetermined magnitude of force. In that regard, the plasmon resonance system may determine a magnitude of the force between the sensor chip and the flow cell based on which of the plurality of measurement indentations are collapsed as determined by the optical system. A first set of one or more of the indentations may collapse at a first known force and a second set of one or more of the indentations may collapse at a higher known force. The system may be configured to stop the actuator when the first set has collapsed but before the second set collapses.

In some embodiments, the optical system may include a photodiode. In other embodiments, the optical system may include a white light emitting diode on a side of the portion of the flow cell and a spectrometer on an opposing side of the portion of the flow cell. The spectrometer may be configured to detect a change in an optical property resulting from the collapse of the portion of the flow cell. For example, the optical property may be absorbance spectra or refractive index.

In another aspect of the invention, a plasmon resonance system for measuring properties of molecular interactions may include a sensor chip, a flow cell, and a thermal control device. The flow cell may include a fluid channel for circulating fluid through an optical path of the sensor chip and the thermal control device may be configured to modulate a temperature of the sensor chip.

The thermal control device is preferably disposed outside the optical path of the sensor chip. For example, the thermal control device may be a ring-shaped Peltier device having an aperture and the optical path may pass through the aperture. Such a Peltier device may be in physical contact with the sensor chip on a first side of the Peltier device. A heat removal device may be disposed on a second side of the Peltier device opposite the first side. The heat removal device may include at least one of a heat sink, a fan, a liquid cooling system, and another Peltier device.

The plasmon resonance system may also include a thermocouple adjacent the first side of the Peltier device and a controller configured to modulate power supplied to the Peltier device based upon a signal from the thermocouple.

In some embodiments, the fluid channel of the flow cell may be configured to provide a sufficient period of exposure to permit fluid in the flow channel to reach a target temperature based on temperature control provided by the thermal control device.

As an alternative or in addition to a ring-shaped Peltier device, the thermal control device may include a continuous thermal control device in thermal contact with a chip holder to control a temperature of the chip holder. In turn, the chip holder may be in thermal contact with the sensor chip such that the thermal control device indirectly controls the temperature of the sensor ship.

In some embodiments, contacting pins may be in electrical communication with the thermal control device. The contacting pins may be positioned and configured to contactingly engage corresponding contacts on a flow cell holder to establish electrical communication between a controller and the thermal control device when a shuttle carrying one of the chip holder and the flow cell is in a docked configuration. The contacting pins may be configured to disengage from the corresponding contacts when the shuttle is moved to an undocked configuration. In this regard, relative movement of the sensor chip toward the flow cell may result in the contacting pins automatically engaging electrical contacts to supply power to the sensor chip.

In another aspect, a plasmon resonance system for measuring properties of molecular interactions may include a sensor chip, a flow cell, a plurality of displacement pumps, and a plurality of valves. The flow cell may include a fluid channel for circulating fluid across a detection region of the sensor chip. The plurality of displacement pumps may each be configurable for fluid communication with the flow cell to circulate the fluid in the fluid channel. The plurality of valves may be used to selectively establish fluid communication between each of the plurality of displacement pumps and the fluid channel.

A first valve may be configured to selectively isolate a first displacement pump from the fluid channel during priming of the first displacement pump via a source port. A second valve may be configured to selectively fluidly connect a second displacement pump to the fluid channel before priming of the first pump. Furthermore, the first valve and the second valve may be configured for simultaneous operation to maintain a substantially constant flow of fluid in the fluid channel as the first valve is closed and the second valve is opened.

The plurality of valves may be configured to direct flow from each displacement pump to a waste port during a period of time after priming the displacement pump and prior to the displacement pumping reaching steady-state operation.

At least one valve of the plurality of valves may be configured to prevent pressure spikes by temporarily directing flow from at least one of the plurality of displacement pumps to a waste port while a downstream valve is operated.

In some embodiments, a first displacement pump of the plurality of displacement pumps is configured to operate at a transit flow rate and a second displacement pump of the plurality of displacement pumps is configured to operate at an analysis flow rate. The analysis flow rate may be less than the transit flow rate.

The plurality of valves may be configured to fluidly connect the first displacement pump to the fluid channel during injection of a sample into the fluid channel. The plurality of valves may also be configured to fluidly isolate the first displacement pump from the fluid channel and fluidly connect the second displacement pump to the fluid channel as the sample approaches the sensor chip.

In another aspect of the invention, a flow cell for a plasmon resonance system may include a first fluid channel, a second fluid channel, and a selector valve. The second fluid channel may extend between a second inlet port and an outlet port. The first fluid channel may extend between a first inlet port and an intersection of the first fluid channel with the second fluid channel. The selector valve may be used to select either the first inlet port or the second inlet port for injection of fluid.

The intersection of the first fluid channel and second fluid channel may be y-shaped to prevent fluid injected through the second inlet port from passing upstream into the first fluid channel.

At least a portion of the first channel and a portion of the second channel may be configured to route fluid across a single sensor spot of a sensor chip. Alternatively or additionally, at least a portion of the first channel may be configured to route fluid across a first sensor spot of a sensor chip and at least a portion of the second channel may be configured to route fluid across a second sensor spot of the sensor chip. At least one physical (e.g., shape) or chemical (e.g., material) property of the first sensor spot may be different than a corresponding property of the second sensor spot.

In another aspect, a method of preparing a flow cell as described above for an assay may include selecting the first inlet port; injecting 1-Ethyl-3-(3-dimethylaminopropyl)-carbodiimide (EDC)/N-hydroxysuccinimide (NHS) through the first inlet port, first fluid channel, and second fluid channel; selecting the second inlet port; injecting a ligand through the second inlet port and second channel; selecting the first inlet port; injecting a blocking solution through the first inlet port, the first fluid channel, and the second fluid channel; and injecting analytes through the first inlet port, the first fluid channel, and the second fluid channel.

In yet another aspect, a method of performing a plasmon resonance assay may include preparing a flow cell as described above; executing the assay; and subtracting at least one reference value obtained by the sensor chip from the first fluid channel from a test value obtained by the sensor chip from the second fluid channel.

In an embodiment, a method of preparing a flow cell for an assay may include selecting the first inlet port; injecting 1-Ethyl-3-(3-dimethylaminopropyl)-carbodiimide (EDC)/N-hydroxysuccinimide (NHS) through the first inlet port, first fluid channel, and second fluid channel; selecting the second inlet port; injecting a first ligand through the second inlet port and second channel; injecting a blocking solution through the second inlet port and second channel; selecting the first inlet port; injecting a second ligand through the first inlet port, the first fluid channel, and the second fluid channel; injecting a blocking solution through the first inlet port, the first fluid channel, and the second fluid channel; and injecting analytes through the first inlet port, the first fluid channel, and the second fluid channel.

In another aspect, plasmon resonance system for measuring properties of molecular interactions may include a sensor chip, a flow cell, and a light emitting diode. The flow cell may include a fluid channel for circulating fluid through an optical path of the sensor chip. The light emitting diode may be disposed on a side of the flow cell opposite the sensor chip.

The light emitting diode may be disposed on a printed circuit board that is selectively removable from the plasmon resonance system. The printed circuit board may include a plug-in socket style fastener. The plasmon resonance system may also include at least one alternative printed circuit board may include a second light emitting diode with at least one property different than the light emitting diode. In this regard, LEDs may be swapped out by selectively replacing the printed circuit board A printed circuit board may include a second light emitting diode. The light emitting diode and the second light emitting diode may both be disposed within an optical path of the sensor chip and may be operated independently of each other.

The flow cell may include a soft portion on a side adjacent the sensor chip and a rigid portion on a side opposite the sensor chip. The rigid portion may include a recess disposed along an optical path extending from the light emitting diode to the sensor chip.

In some embodiments, the printed circuit board may include an ultraviolet light emitting diode.

BRIEF DESCRIPTION OF DRAWINGS

Figure 6:
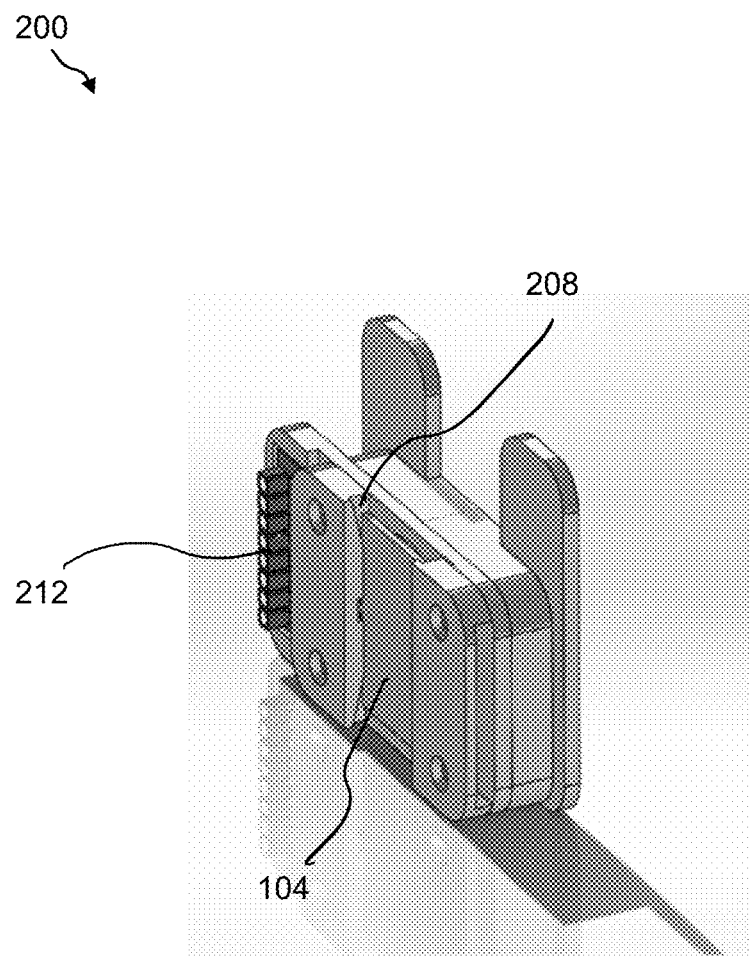
Figure 7:
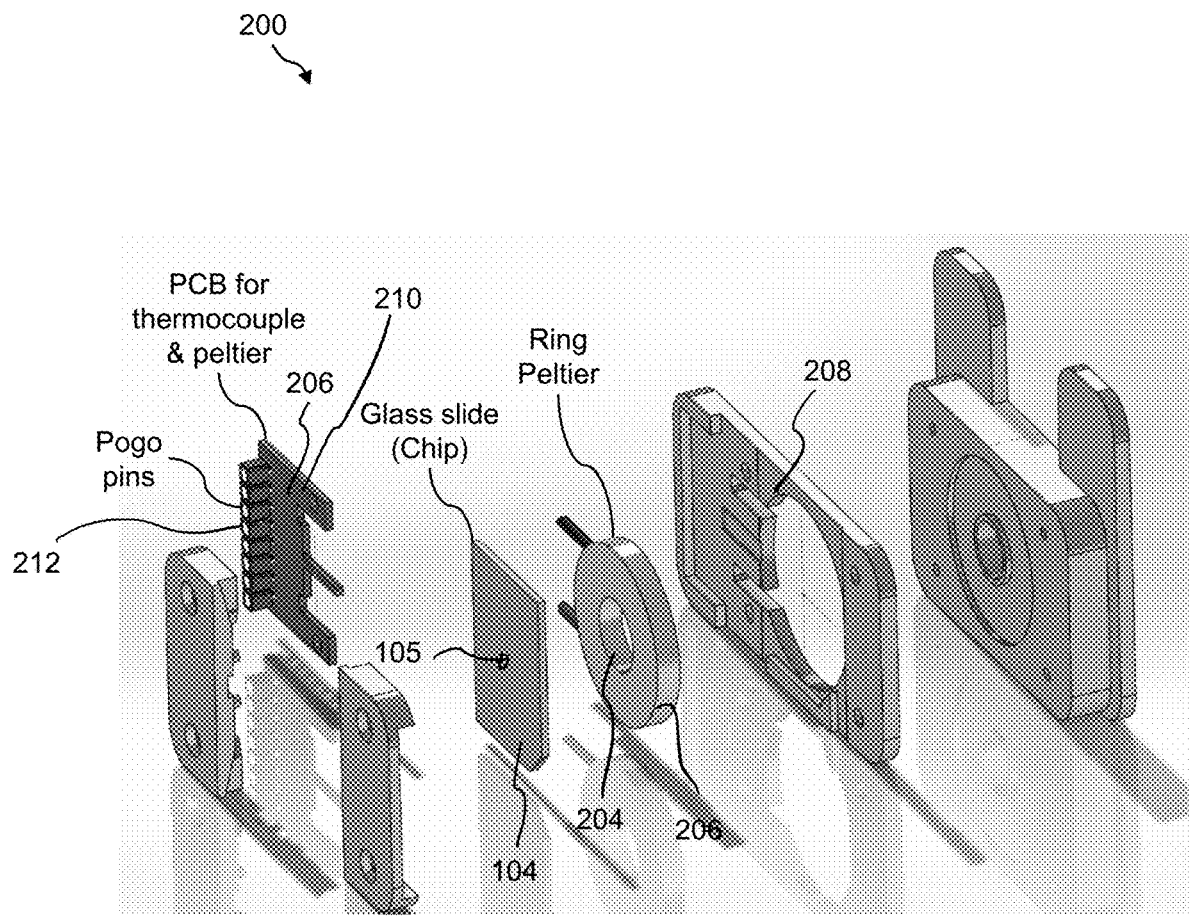
Figure 13:
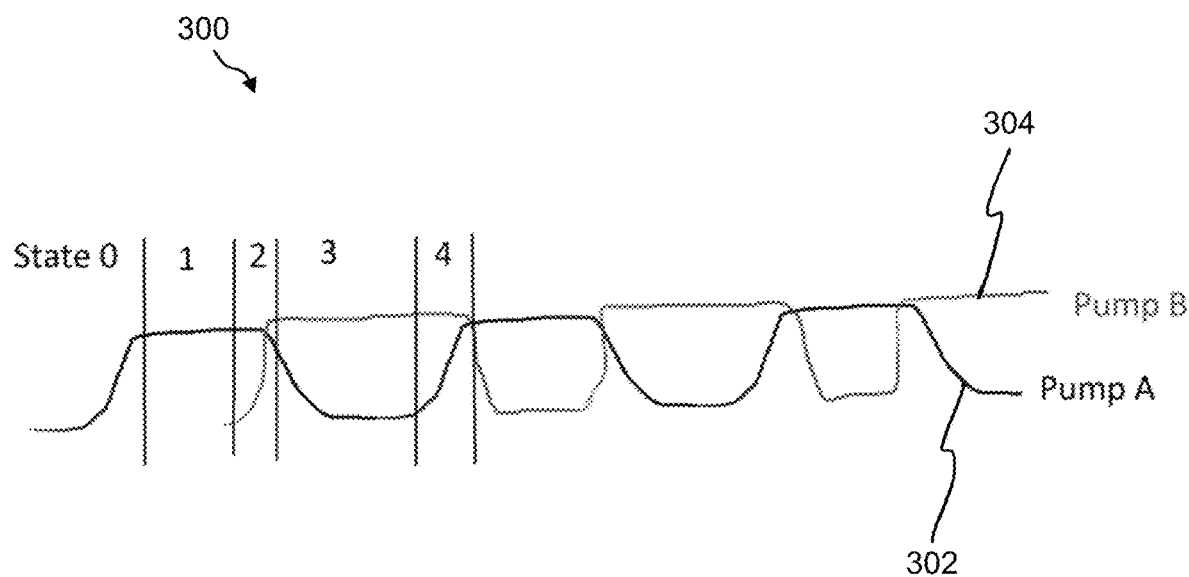
Figure 14:
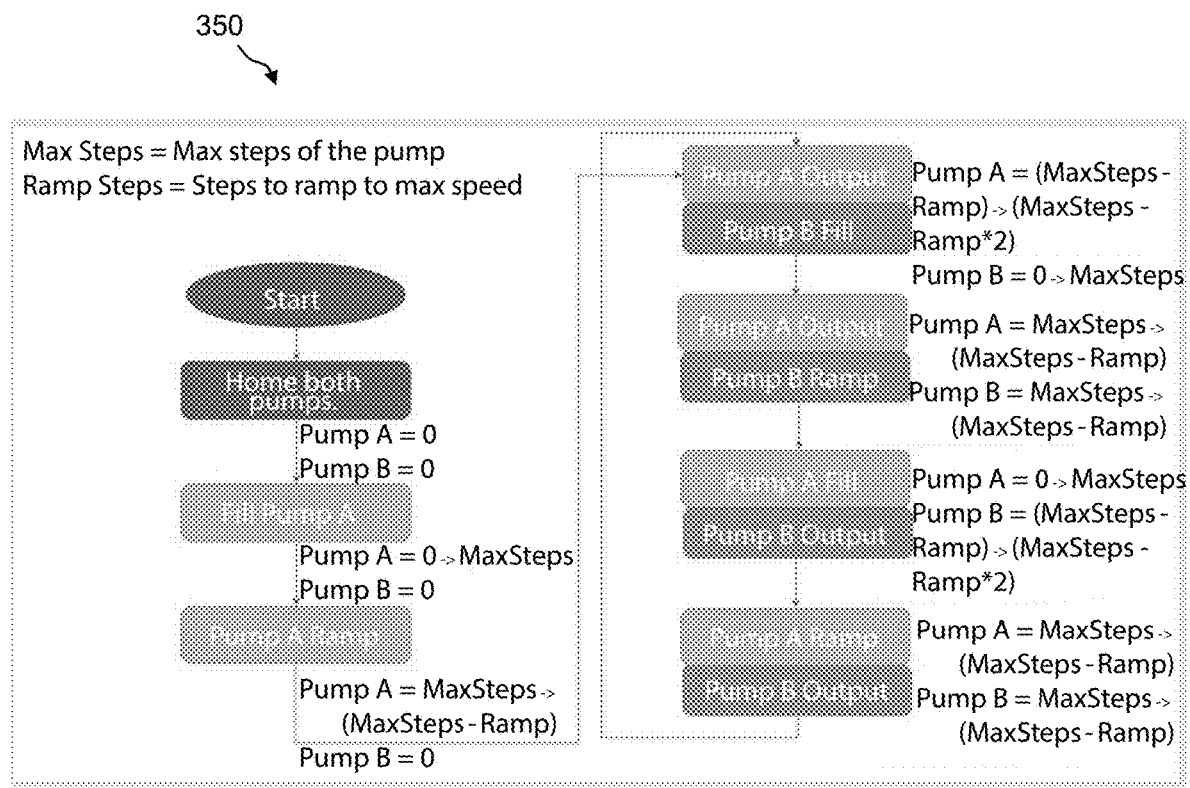
Figure 15:
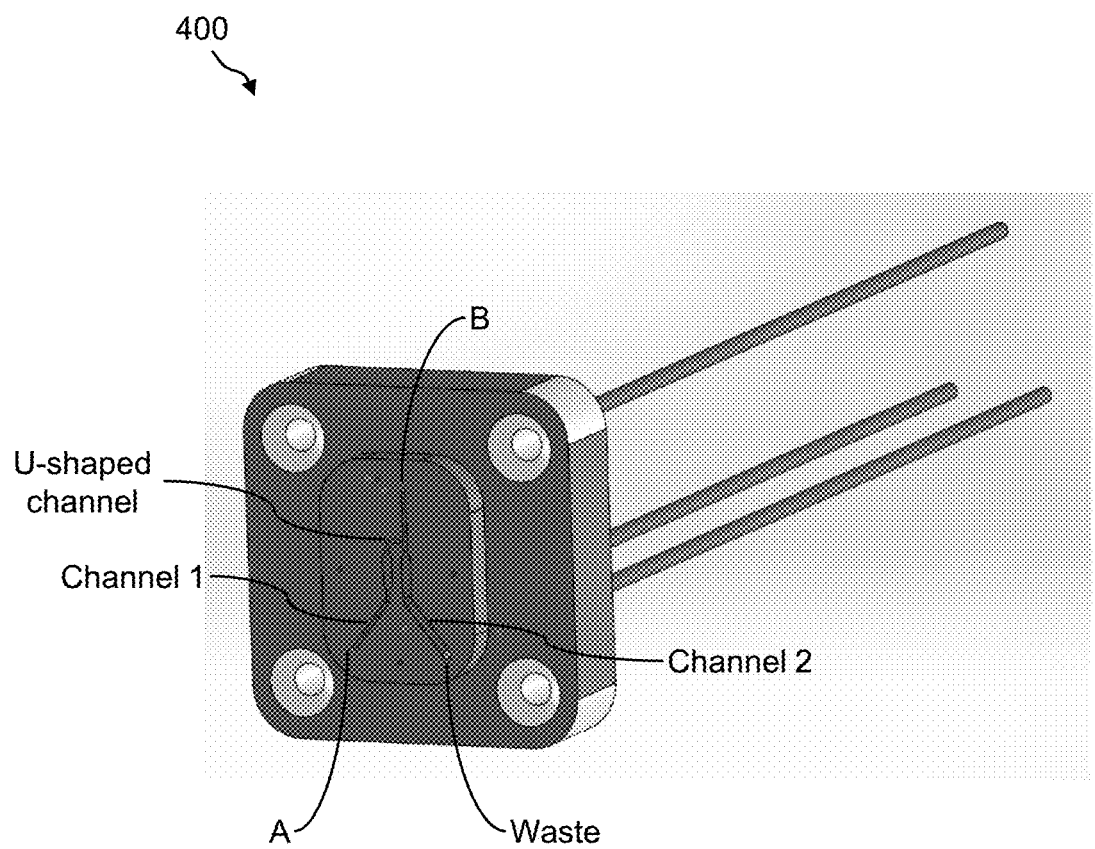
Figure 16:
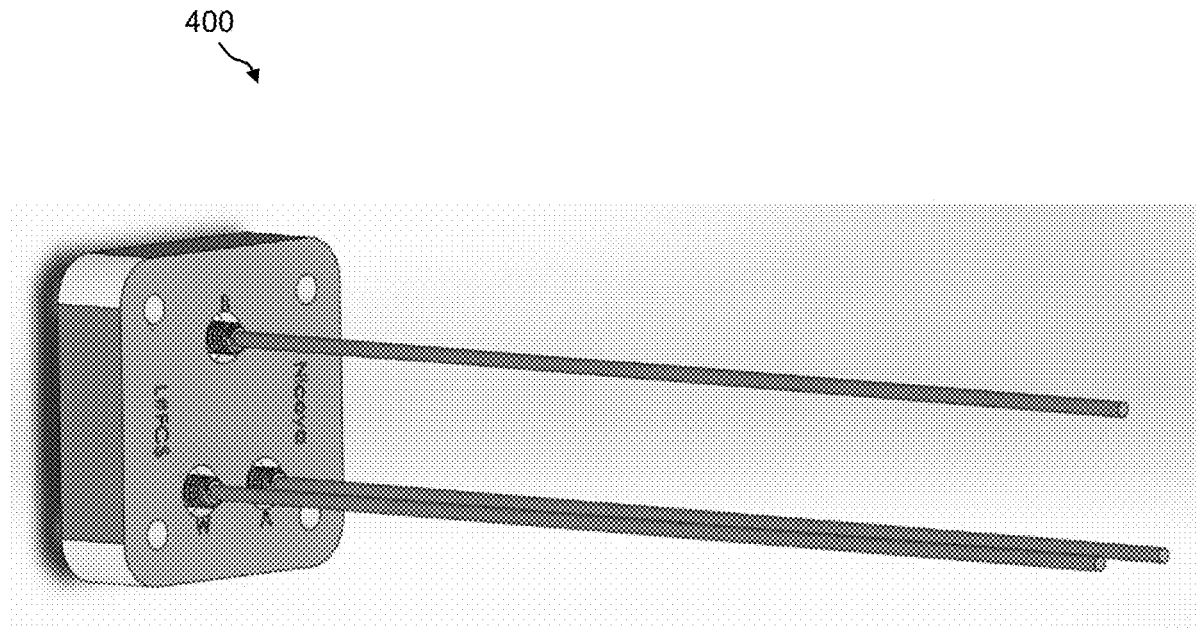
Figure 17:
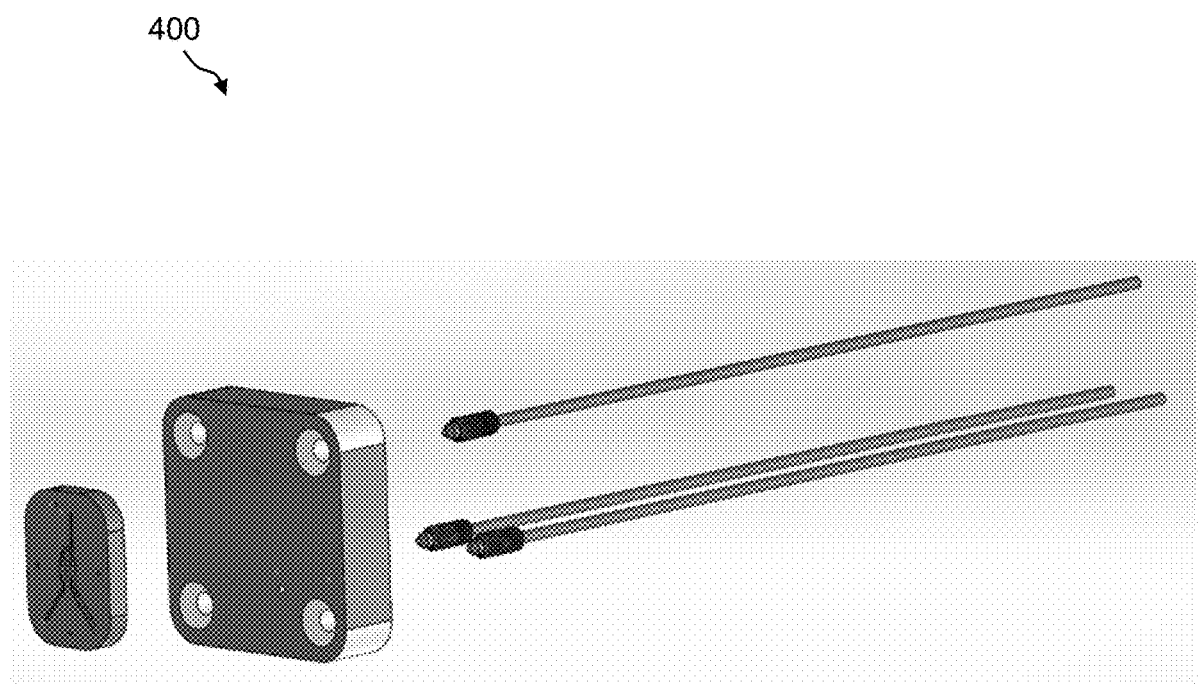
Figure 18B:
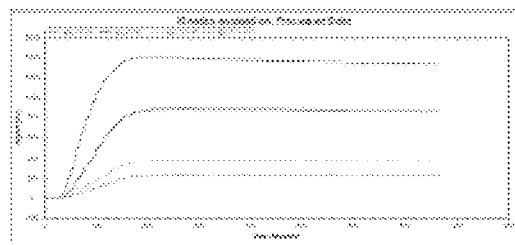

Having thus described the presently disclosed subject matter in general terms, reference will now be made to the accompanying Drawings, which are not necessarily drawn to scale, and wherein:

FIG. 1, FIG. 2, FIG. 3, FIG. 4, and FIG. 5 show various views of an embodiment of a clamp assembly of the presently disclosed PR system, instrument, and/or device;

FIG. 6 and FIG. 7 show a perspective view and an exploded view, respectively, of an embodiment of a ring Peltier chip holder 200 of the presently disclosed PR system, instrument, and/or device;

FIG. 8 through FIG. 12 show schematic diagrams of various states of an embodiment of two displacement pumps for constant flow delivery to a microfluidic device of the presently disclosed PR system, instrument, and/or device;

FIG. 13 shows a state diagram of an embodiment of two displacement pumps with respect to speed;

FIG. 14 shows a flow diagram of an embodiment of a pump procedure for operating the two displacement pumps;

FIG. 15, FIG. 16, and FIG. 17 show a front view, a back view, and an exploded view, respectively, of an embodiment of a flow cell that includes a dual channel LSPR sensor; and FIG. 18A and FIG. 18B show an example of results from a two-channel instrument that uses the dual channel LSPR sensor shown in FIG. 15, FIG. 16, and FIG. 17 for protein interaction analysis.

FIG. 19 through FIG. 22 show schematic diagrams of an embodiment of various states of two displacement pumps and valves for a rapid buffer exchange process.

DETAILED DESCRIPTION

The presently disclosed subject matter now will be described more fully hereinafter with reference to the accompanying Drawings, in which some, but not all embodiments of the presently disclosed subject matter are shown. Like numbers refer to like elements throughout. The presently disclosed subject matter may be embodied in many different forms and should not be construed as limited to the embodiments set forth herein.

In some embodiments, the presently disclosed subject matter provides a plasmon resonance (PR) system, instrument, and/or device and configurations thereof for measuring molecular interactions. In some embodiments, the PR system, instrument, and/or device may be a localized surface plasmon resonance (LSPR) system, instrument, and/or device for measuring binding kinetics. In other embodiments, the PR system, instrument, and/or device may be a surface plasmon resonance (SPR) system, instrument, and/or device for measuring binding kinetics.

The presently disclosed PR system, instrument, and/or device may include, for example, force feedback for reliable flow cell sealing, optical feedback for reliable flow cell sealing, local thermal control of an LSPR chip (e.g., using a ring Peltier or a continuous Peltier), dual displacement pumps for constant flow delivery to a microfluidic device, a dual channel LSPR sensor, and any combinations thereof.

A first embodiment includes a PR system, instrument, and/or device including force feedback for reliable flow cell sealing. For instance, SPR instruments may include a glass or plastic sensor chip to be fluidically sealed against a flow cell. This flow cell can be a permanent part of the SPR instrument, and the glass chip reversibly and selectively sealed against the flow cell. In turn, a fluidic system may be provided to provide fluid to the flow cell. Flow cell materials are typically made of soft polymers like Polydimethylsiloxane (PDMS) or Viton. When a glass sensor chip is to be sealed against a PDMS flow cell, there is a high chance for failure to happen as a precise sealing force needs to be applied. However, different flow cells and sensor chips can have different thicknesses. This may result from unique flow cell/sensor chip designs and/or from varying tolerances of the flow cell/sensor chip design. Accordingly, relying purely on movement of the flow cell and sensor chip relative to one another by a predetermined distance is unreliable. For instance, if too much force is applied the PDMS channel may collapse, if too little is applied, and the flow cell may leak.

In one embodiment of a SPR system, instrument, and/or device, active force feedback may be used to keep constant force acting between the flow cell and sensor chip, regardless of mechanical intolerance in the sensor chip or flow cell. For instance, with reference to FIGS. 1-5, a clamp assembly 100 is shown that includes a linear stage 102 that may be used to move the sensor chip 104 between a docked and undocked position relative to an open faced flow cell 106. For instance, the linear stage 102 may controllably move a shuttle 108 with which the sensor chip 104 is supportively engaged. The flow cell 106 may be mounted on a stationary pedestal 110 and the shuttle 108 may be displaceable relative thereto. In this regard, the shuttle 108 may move between a docked position shown in FIG. 1 and FIG. 4 and an undocked position shown in FIG. 2 and FIG. 3. While the embodiments described herein provide movement of the sensor chip 104, it may be appreciated that any arrangement in which the flow cell 106 and the sensor chip 104 undergo relative movement to contactingly engage the sensor chip 104 and flow cell 106 to provide sealing engagement therebetween may be provided. This may include movement of the flow cell 106, movement of the sensor chip 104, and/or movement of both the flow cell 106 and the sensor chip 104.

Further, a force acting between the sensor chip 104 and the flow cell 106 may be measured using a load sensor 112 (shown in FIG. 1) mounted on the back of the flow cell 106. In this regard, the flow cell may be free floating relative to the stationary pedestal 110 such that the force acting between the sensor chip 104 and the flow cell 106 may be measured by the load sensor 112 when the linear stage 102 advances the shuttle 108 to the docked position to contactingly engage the flow cell 106 with the sensor chip 104. For instance, the linear stage 102 may comprise a controllable electric motor (e.g., a stepper motor or the like) that may control the relative position of the flow cell 106 and the sensor chip 104. Other linear actuators may be utilized without limitation. In any regard, the electric motor may be activated to contactingly engage the flow cell 106 with the sensor chip 104 until a desired force as measured by the load sensor 112 is achieved. That is, the linear stage 102 can be moved to the dock position until the target "sealing force" is measured on the load cell 112. Further, this could apply to any type of microfluidic chip or sensor with a removable face. Further, the load cell 112 can also be used to detect leaks in the system as the force acting between the flow cell 106 and the sensor chip 104 may change if there is a leak.

Figure 1:
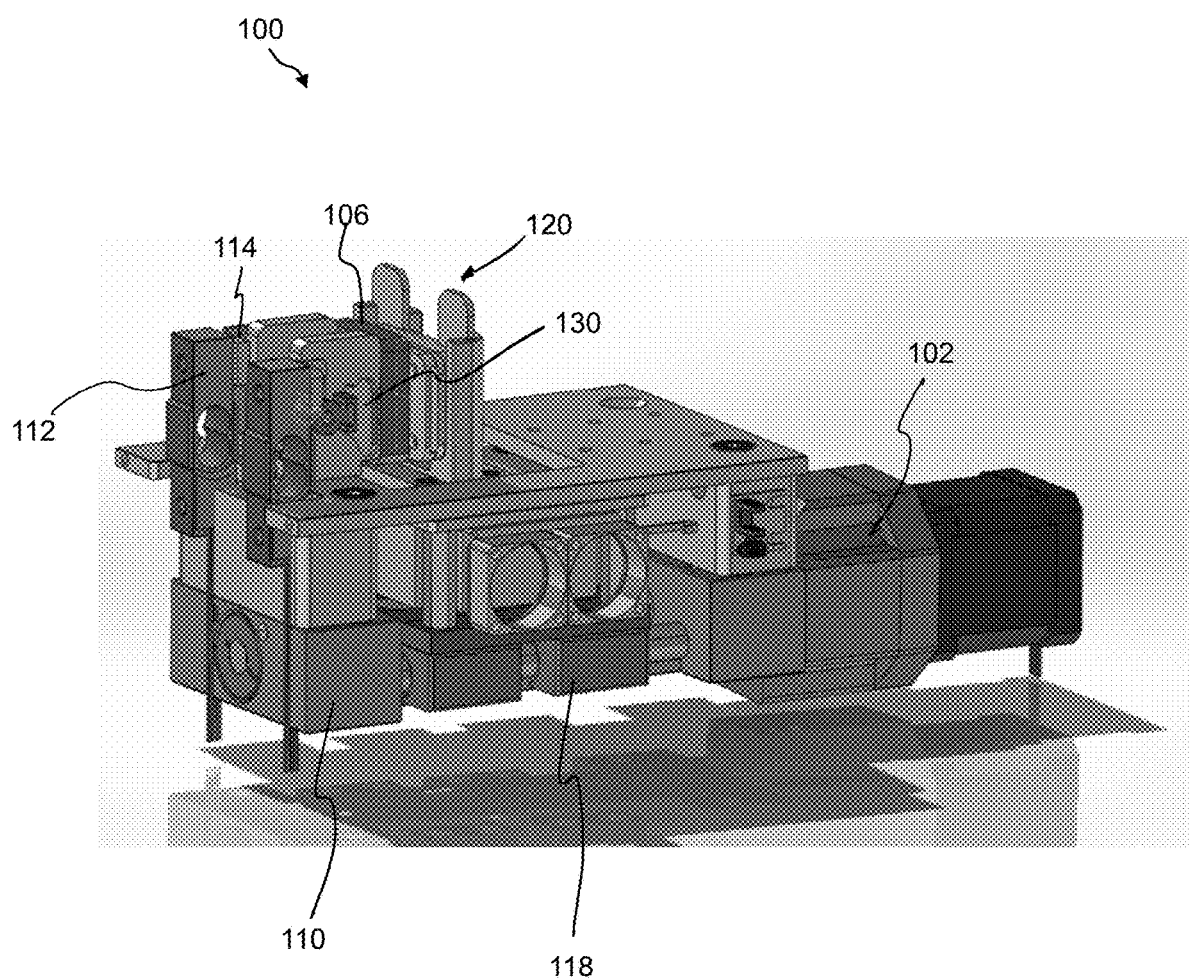
Figure 2:
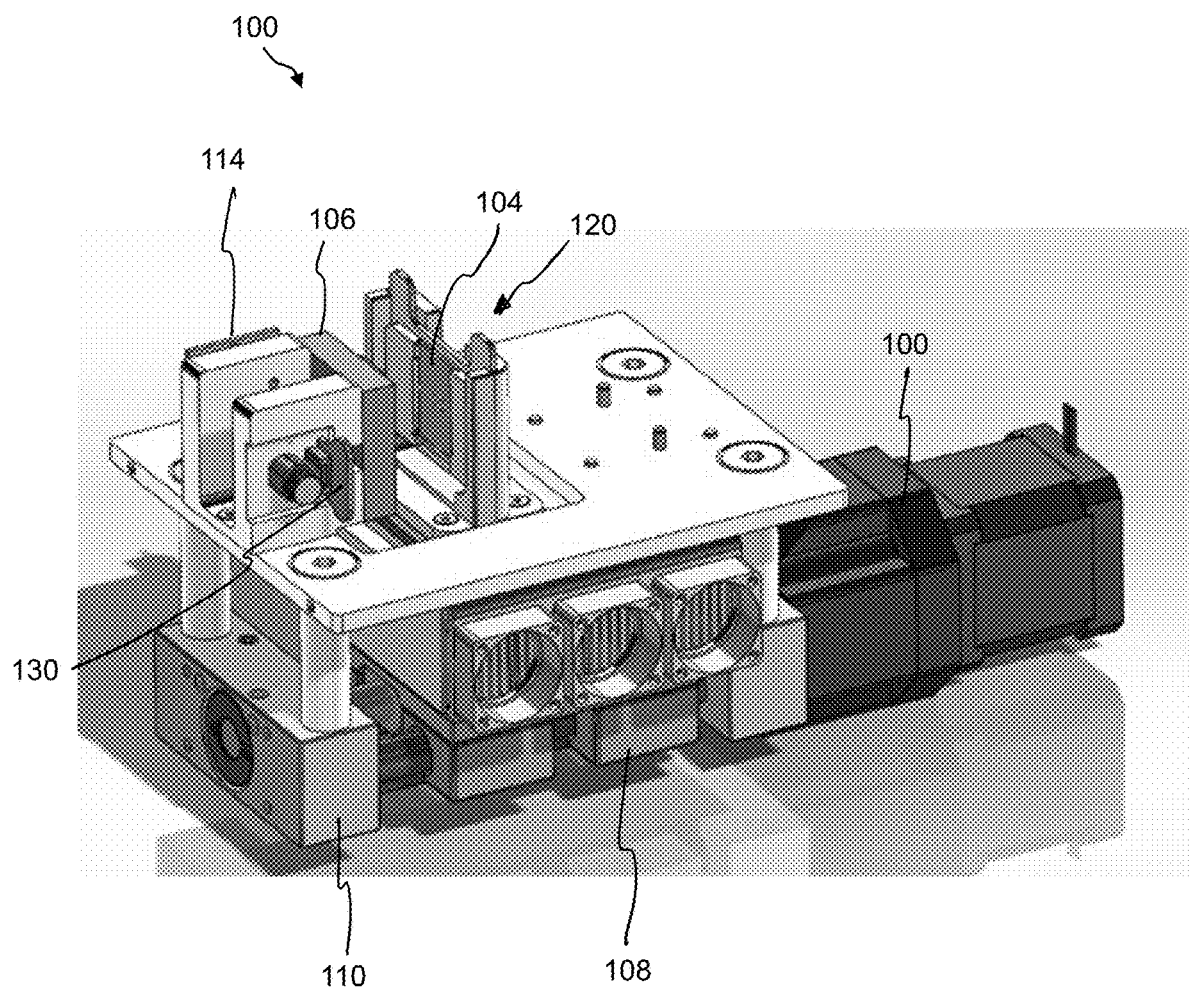
Figure 3:
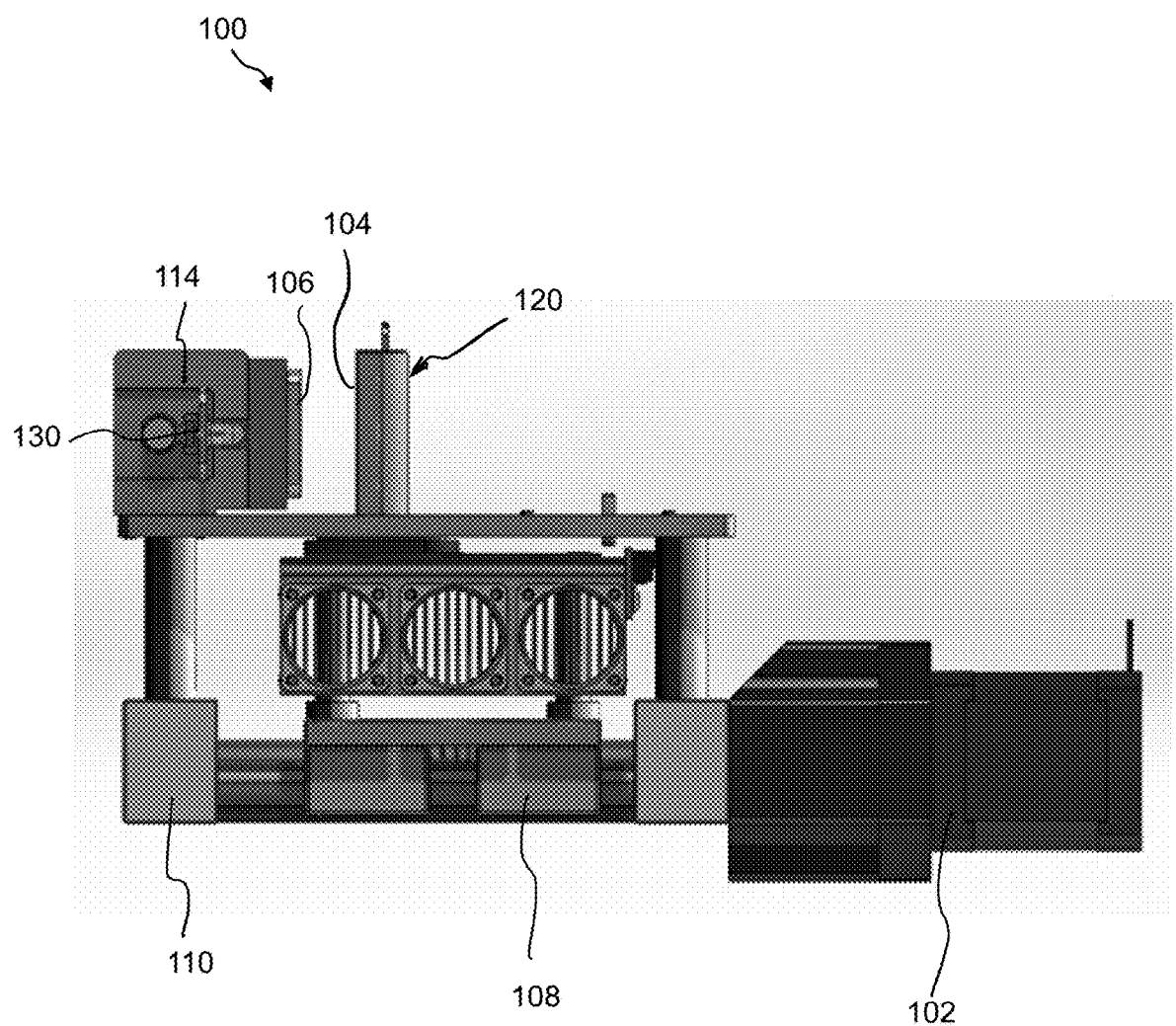
Figure 4:
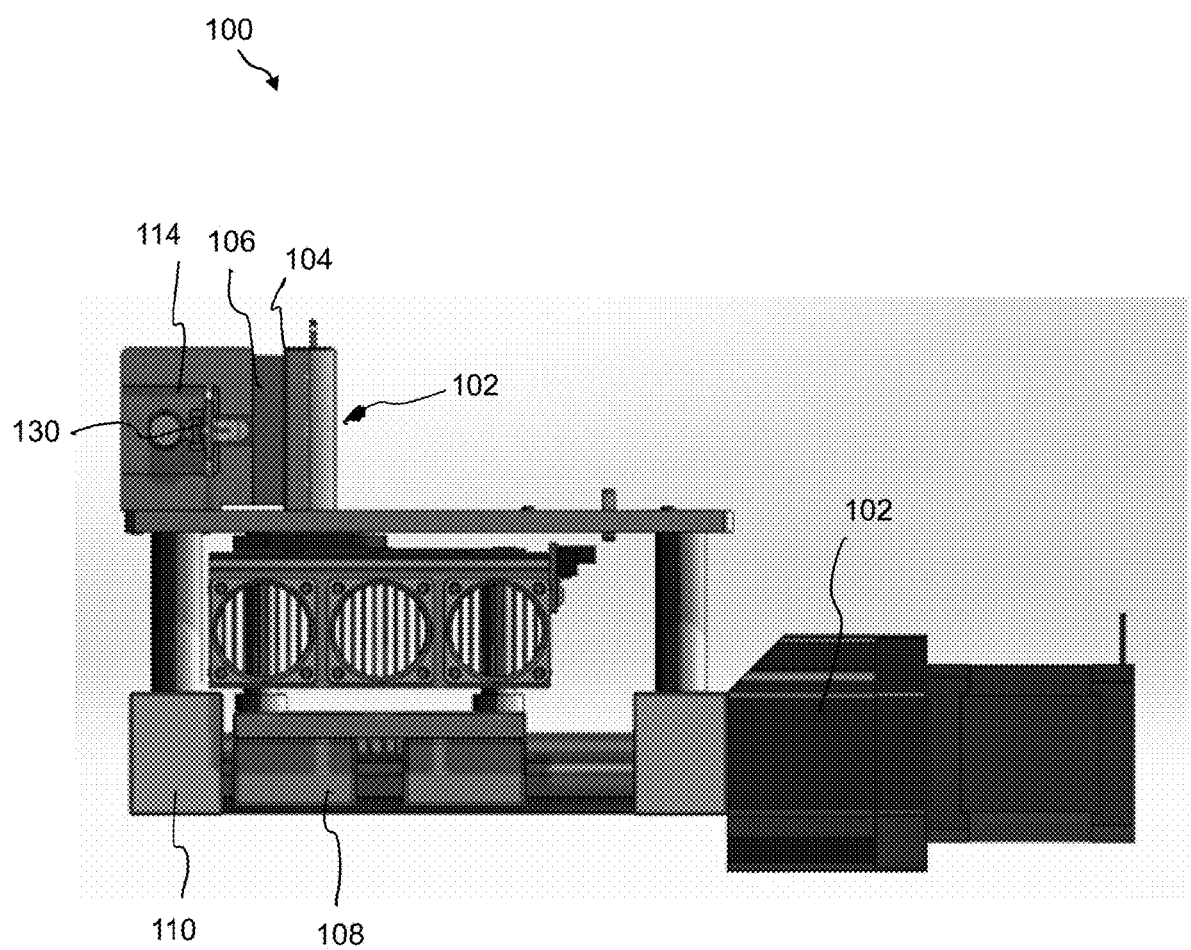
Figure 5:
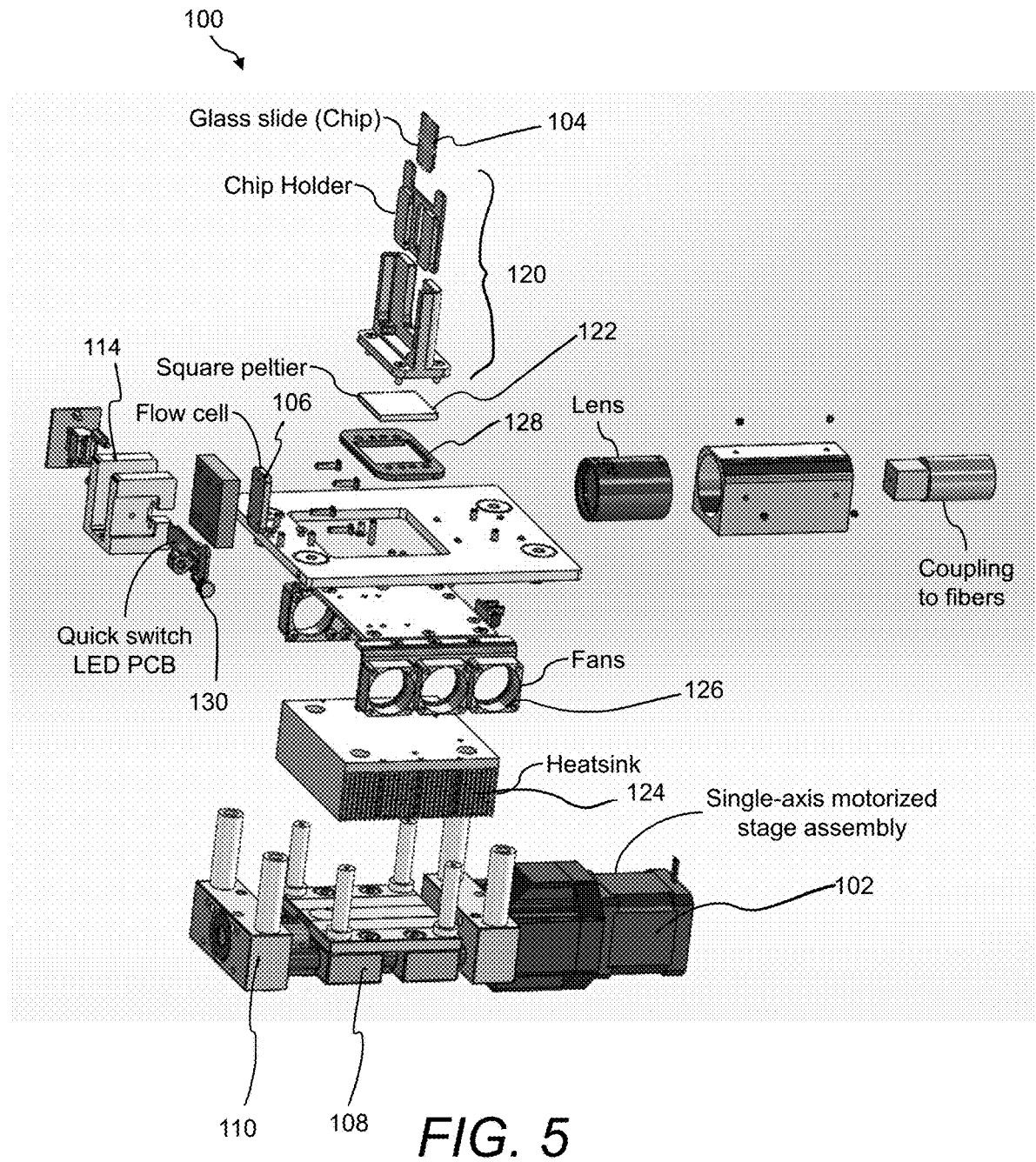

FIG. 1 and FIG. 2 show perspective views of the clamp assembly 100 with and without load cells, respectively. While the load cells 112 are not depicted in FIGS. 2-5, it may be appreciated that the load cells 112 may be provided although not depicted. FIG. 3 and FIG. 4 show perspective views of the clamp assembly 100 in the "opened" or "undocked" position and in the "closed" or "docked" position, respectively. FIG. 5 shows an exploded view of the clamp assembly 100.

Additionally or alternatively, an embodiment of a PR system, instrument, and/or device may include optical feedback for reliable flow cell sealing. The SPR system, instrument, and/or device having optical feedback may be similar to the SPR system, instrument, and/or device described above except that the embodiment comprising optical feedback may not include any additional hardware, such as the load cell 112, to provide feedback on clamping force.

Rather, the embodiment comprising optical feedback may employ optical measurement to determine when sufficient engagement between the sensor chip 104 and the flow cell 106 has been achieved (e.g., to effectuate sealing between the sensor chip 104 and the flow cell 106). For instance, in the SPR system, instrument, and/or device, the PDMS flow cell 106 may contain a channel that is 100 μm in depth. As the flow cell may comprise a relatively soft material, the channel may be deformable upon application of a force between the flow cell 106 and the sensor chip 104 such that the channel in the flow cell 106 may collapse under application of a given force. That is, after a certain clamp force has been applied between the glass chip/PDMS flow cell, the 100 μm channel may collapse against the glass slide. This is may be referred to as the "collapse force." Further, the optical system used for SPR may be a white light LED and a spectrometer. The optical system may interrogate the area inside the flow cell during movement between the flow cell 106 and the sensor chip 104. When the channel it is not collapsed, the interface between the flow cell 106 and the sensor chip 104 may have a certain optical property (e.g., absorbance spectra) that can be measured with the spectrometer. This optical property (e.g., absorbance spectra) may change upon application of force between the flow cell 106 and the sensor chip 104, for example, as a result of the collapse of the channel.

The change in the optical property may be due to a change in a refractive index (RI) of the interface between the flow cell 106 and the sensor chip 104. For instance, before the collapse, light may pass through the flow cell material, material present within the channel (e.g., air), and through the sensor chip material. This path may have a given RI. This path may include a high RI material (e.g., the PDMS of the flow cell 106), a low RI material (e.g., air in the channel), and a high RI material (e.g., the glass of the sensor chip 104). This optical path may create a series of reflections. However, when the channel is collapsed, light may pass directly from a high RI material (e.g., the PDMS of the flow cell 106) to a high RI material (e.g., the glass of the sensor chip 104), so the amount of light reflection is reduced, thus changing the RI of the interface. This difference in the RI can be detected on the spectrometer and used to identify when the channel collapses under the application of the collapsing force (or at a collapsing distance). Once this has been reached, the linear stage 102 can be backed off by a set distance. In this way, the clamping force between the sensor chip 104 and flow cell 106 can be calibrated and remain consistent between instruments/flow cells.

Further, the PDMS material of the flow cell 106 can include one or more measurement indentations of varying depths that may be provided at increments of, for example, 10 μm in depth. In turn, the collapse of these measurement indentations may indicate a sufficient clamping force has been achieved. Detection of the measurement indentation collapse can be performed similarly to the channel collapse via the optical system and spectrometer or through a parallel photodetection system such as a photodiode. In this regard, the measurement indentations may allow for measurement of the application of the force between the flow cell 106 and the sensor chip 104 by detecting which of the various measurement indentations have collapsed upon advancement of the linear stage 102. This may allow for direct optical calibration of the clamping force applied between the flow cell 106 and the sensor chip 104.

In an additional embodiment, a PR system, instrument, and/or device may include local thermal control of an LSPR chip. Such control may be achieved by introduction of a thermal control device that may include a thermoelectric device including, but not limited to, a ring Peltier device (e.g., a Peltier device with a hole in the middle).

In an LSPR system, instrument, and/or device, it may be desirable to control the temperature of the sensor chip 104 (e.g., LSPR chip) in order to have stable measurements and also to perform thermodynamic measurements. For example, one may use a thermal control device to provide local control of the temperature of a sensor chip 104 (e.g., providing heating or cooling of the sensor chip 104). Such a thermal control device may preferably allow maintaining an optical path to allow transmission measurement of the LSPR signal, while also being positioned near or in contact with the sensor chip 104 to provide increased control of the temperature of the sensor chip 104. FIG. 6 and FIG. 7 show a perspective view and an exploded view, respectively, of an example of a chip holder 200 that comprises a ring Peltier device 204 for use in an embodiment of a LSPR system, instrument, and/or device. The chip holder 200 may be provided in place of the chip holder 120 shown in FIGS. 1-5.

In the chip holder 200, the ring Peltier device 204 may be aligned with the center of the sensor chip 104 such that the LSPR sensor 105 may be aligned with the aperture 204 of the ring Peltier device 204, thus allowing for a transmission measurement to be conducted. That is, the thermal control device may be provided in contact with the sensor chip 104, yet not extend into the optical path of the PR device. Further, in another embodiment, a reflection mode system may be provided that includes a Peltier device mounted to the chip holder 200 on a side opposite the optical measurement system.

In the chip holder 200, the side of the Peltier device 204 in contact with the sensor chip 104 may be referred to as the "front side" of the Peltier device 204. As the Peltier device 204 may be in contact with the sensor chip 104, the Peltier device 204 may control the temperature of the sensor chip 104. The temperature control may be based on a set temperature that may be selected by a user. Heat can be removed from the opposite side of the Peltier device 204 that is not in contact with the sensor chip 104, which may be referred to as the "back side" of the Peltier device 204. Such heat removal may use any one or more of many techniques such as heat sinks on the back of the Peltier device 204 with a fan on the side that is not in the path of the optics, heat pipes to move the heat to another area outside of the optical path attached to a heat sink/fan setup, a liquid cooling system, or another Peltier device connected outside of the optical path but in thermal contact with the back side of the Peltier device 204. It may be advantageous to remove heat from the back side of the Peltier device 204 or else thermal runaway may occur, or the dynamic range of the temperature operation may be severely limited.

In the chip holder 200, a thermocouple 206 may be provided adjacent to the "front side" of the Peltier device 204 in order to measure the temperature, so that a controller can precisely control the Peltier device 204 temperature by modulating the power to the Peltier device 204 (e.g., through a computer controller such as a PID control). That is, a user can set the temperature and the PID/thermocouple may ensure precise temperature control of the thermal control device, and in turn, the sensor chip 104.

In the chip holder 200, it may be advantageous to provide a fluid channel in the flow cell 106 of sufficient length such that the fluid flowing through the flow cell 106 may attain the desired temperature controlled by the Peltier device 204 once the fluid reaches the LSPR sensor spot 105 (i.e., where the optics interrogate the sensor). Accordingly, the fluidic inlet of the flow cell 106 may be sufficiently long that at the highest flow rates the fluid reaches the set temperature prior to being interrogated. For instance, if the fluidic inlet portion exposed to the portion of the chip holder 200 that is temperature controlled by the Peltier device 204 is too short, the fluid may not reach the set temperature.

In the chip holder 200, it is preferable to be able to easily remove the sensor chip 104, but it is also desirable for the ring Peltier device 204 to be in contact with the sensor chip 104 in order to maximize thermal efficiency. In this regard, the chip holder 200 may comprise a removable sensor chip that is selectively removable from the chip holder 200. For instance, the chip holder 200 may define a slot 208 for receipt of the sensor chip 104 and Peltier device 204. The Peltier device 204 may be permanently disposed in the slot 208. Moreover, the slot 208 in the chip holder 200 may allow the sensor chip 104 to be removed or inserted (e.g., the sensor chip 104 may be slidably inserted into the slot 208 for contacting engagement with the Peltier device 204 provided in or adjacent to the slot 208).

In addition, the chip holder 200 may include a printed circuit board 210 that includes electronics including contacts for establishing electrical communication with the chip holder 200 (e.g., for electrical communication with the Peltier device 204, thermocouple 206, etc.). The printed circuit board 210 may include self-contacting pins 212, such as pogo pins, on the side which are an electrical communication with the Peltier device 204 and/or the thermocouple 206. Accordingly, when the chip holder 200 is placed onto the shuttle 108 and the shuttle 108 is disposed in the docked position, the self-contacting pins 212 may contactingly engage corresponding contacts on the flow cell holder 114, thereby establishing electrical communication between the clamp assembly 100 and the chip holder 200 that may facilitate electrical communication between a controller and the Peltier device 204 and/or the thermocouple 206. In this way, the Peltier device 204 and/or the thermocouple 206 may be in contacting engagement with the sensor chip 104, but the sensor chip 104 can be easily removed by the user without having the constraint of wires being attached to the sensor chip holder 200.

In an alternative embodiment of a PR system, instrument, and/or device including local thermal control of an LSPR chip, such as, but not limited to, a continuous thermal control device (e.g., a Peltier device without a hole in the middle) may be provided in relation to the sensor chip 104 for control of the temperature of the sensor chip 104. In such an embodiment, the Peltier device may be disposed apart from the optical path of the device, but adjacent to the sensor chip 104 for controlling the temperature of the sensor chip 104.

For instance, a thermal control solution in this embodiment may include a Peltier device 122 located adjacent (e.g., below) the sensor chip holder 120 but in thermal contact with the chip holder 120 as best shown in FIG. 5. The Peltier device 122 may be in contact with the sensor chip holder 120 and may provide indirect temperature control of the sensor chip 104 by controlling the temperature of sensor chip holder 120. The opposite side of the Peltier device 122 may be connected to a heat sink 124, or other thermal management device such as a heat pipe or another Peltier to remove heat from the Peltier device 122. The heatsink 124 may include fans 126 to assist in thermal management of the Peltier device 122.

While the Peltier device 122 that is disposed for control of the temperature of the chip holder 120 without direct contact of the sensor chip 104 may be less thermally efficient than the ring Peltier device 204 in direct contact with the sensor chip 104, the Peltier device 122 may be simpler to implement because the Peltier device 122 may not have to be removed from the instrument with the sensor chip holder 120. The Peltier device 122 may be in thermal contact between the chip holder 120 on a first side thereof and the heatsink 124 on a second side thereof with thermal paste or thermal adhesive. A spacer 128 (e.g., comprising Delrin or other thermally insulating material) may be used to increase the likelihood that pressure is not placed directly on the Peltier device 122, to ensure the sensor chip holder 120 can be held extremely flat relative to the flow cell 106 (which may be important for flow cell sealing), and to provide thermal insulation between the top and bottom sides of the Peltier device 122. A thermocouple (not shown) may be located in close proximity to the sensor spot of the sensor chip 104 and a controller (e.g., executing a PID algorithm) may be used to precisely control the temperature of the sensor spot by control of the Peltier device 122.

Another embodiment of a PR system, instrument, and/or device may include dual displacement pumps for constant flow delivery to a microfluidic device. For many microfluidic devices, like those employed in SPR sensing, it may be advantageous to have constant flow rate with low noise and very low flow rates (e.g., down to 0.1 µl/min) up to higher flow rates of 200 µl/min to provide buffer/sample delivery to the sensor chip or active area. Displacement pumps can provide the above specifications but may have a limited volumetric capacity (e.g. a volumetric capacity of 1 ml, while typical SPR assays and other applications require tens of mL of volume to perform an analysis).

In an embodiment of the SPR system, instrument, and/or device, a plurality of displacement pumps may be provided that are each selectively capable of providing fluid in the microfluidic device so that one pump can be filled while the other pump is pumping fluid through the SPR system. Accordingly, this may provide a continuous pumping solution that allows for larger volumetric flow through the SPR system while maintaining continuous flow rates with low noise. In this pump configuration, the ramp time of the pump, in which the flow rate from the pump increases over time association with the motor of the pump ramping to speed, may be accounted for by purging to waste before switching which pump is actively providing fluid to the SPR system. Absent the purging to waste, there may be a speed transient in which the flow rate to the SPR system varies, which may be undesirable. The control of which pump is providing fluid to the SPR system as well as purging operations to maintain consistent flow rates may be accomplished using valves like a solenoid valve on each of the pumps that allow a pump to either pump into the flow cell or pump to waste. Operation of a dual pump system to provide constant flow rates beyond the volumetric capacity limits a single pump are described in greater detail below.

In one example shown in FIGS. 8-12, two displacement pumps, pump A 302 and pump B 304, may be provided in an embodiment of the SPR system, instrument, and/or device. Accordingly, FIG. 8 through FIG. 12 show schematic diagrams of various states of pump A 302 and pump B 304 in which bolded lines reflect flow and dotted lines reflect open path but no flow. In the schematics, a plurality of source ports 306 may be provided to respective fluid sources. Additionally, a waste port 308 may be provided. For each of these ports, a corresponding valve may be provided to selectively establish fluid communication with a given port. In addition, pump A 302 may have an input valve 312 and an output valve 314. Similarly, pump B 304 may include an input valve 316 and an output valve 318. An output port 310 that may be in fluid communication with the SPR system may be provided.

Figure 8:
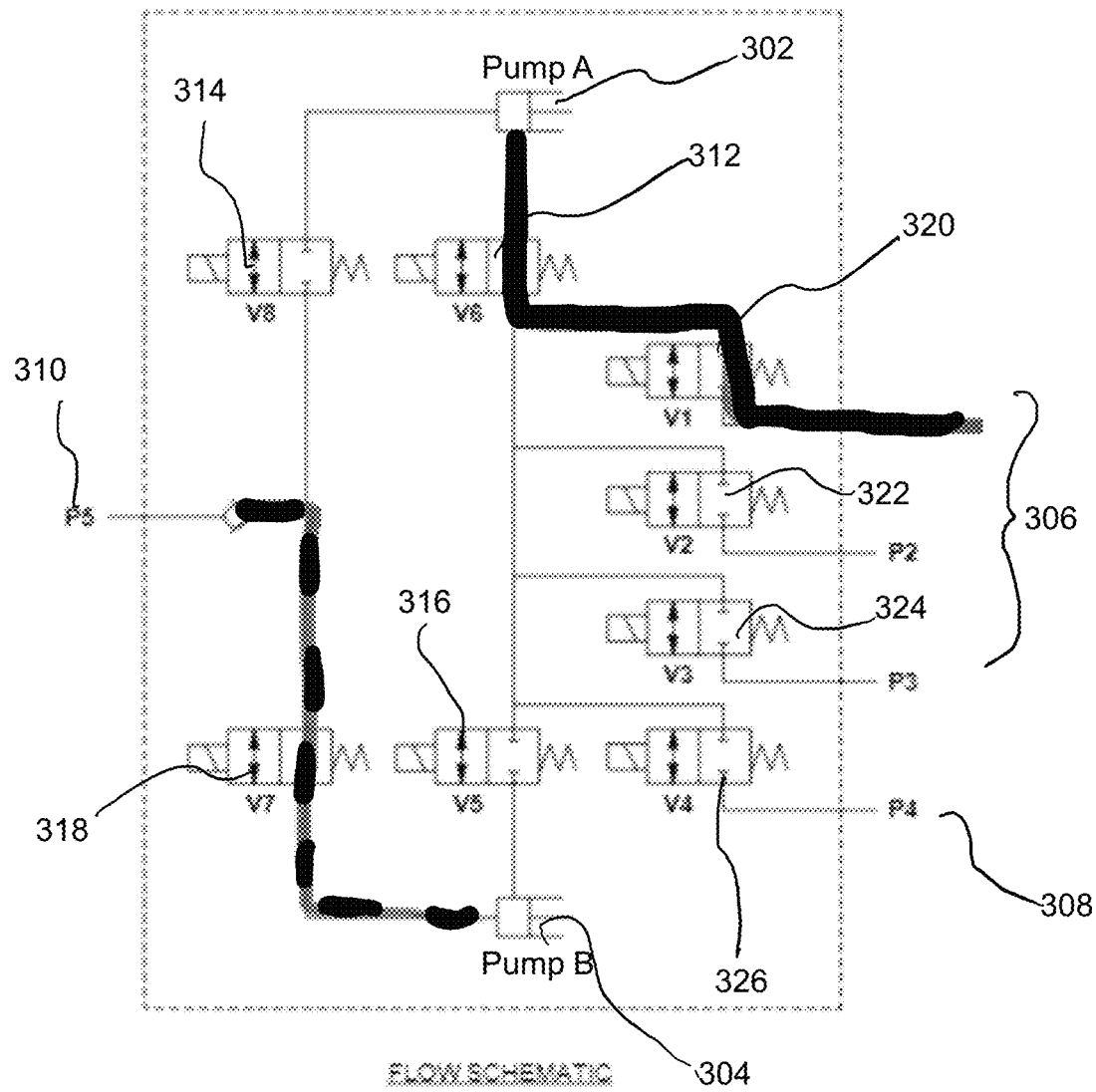
Figure 9:
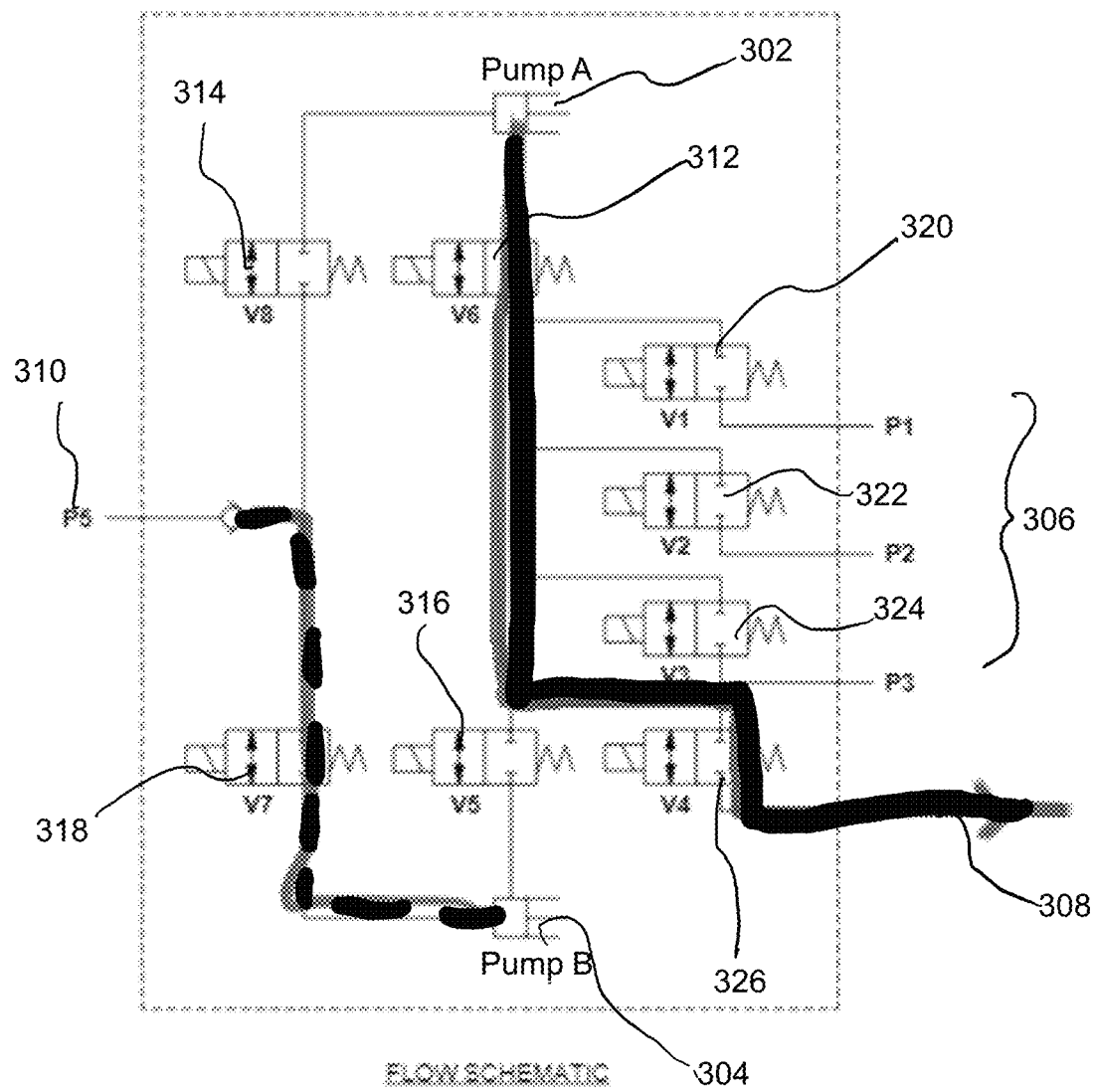
Figure 10:
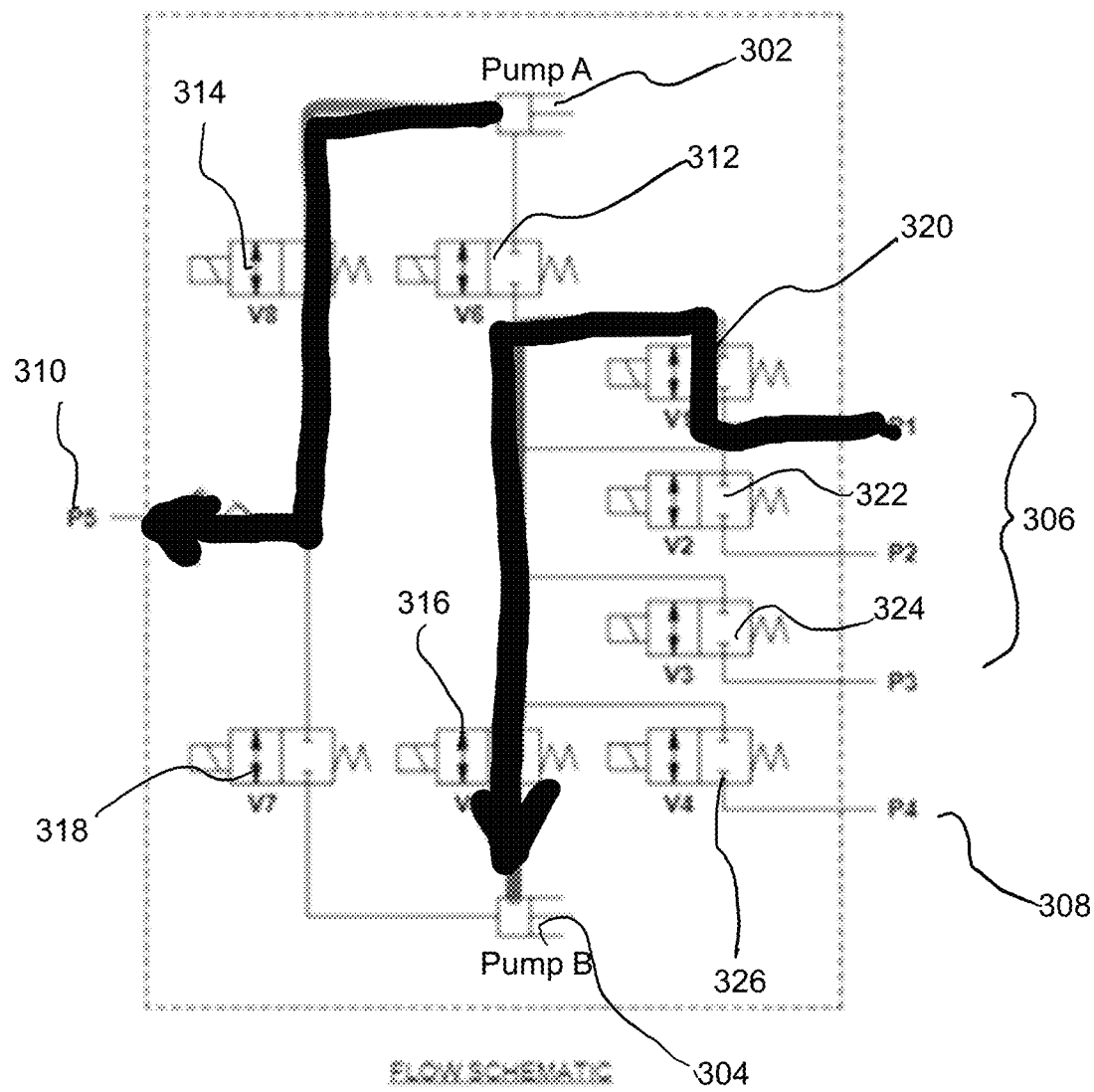
Figure 11:
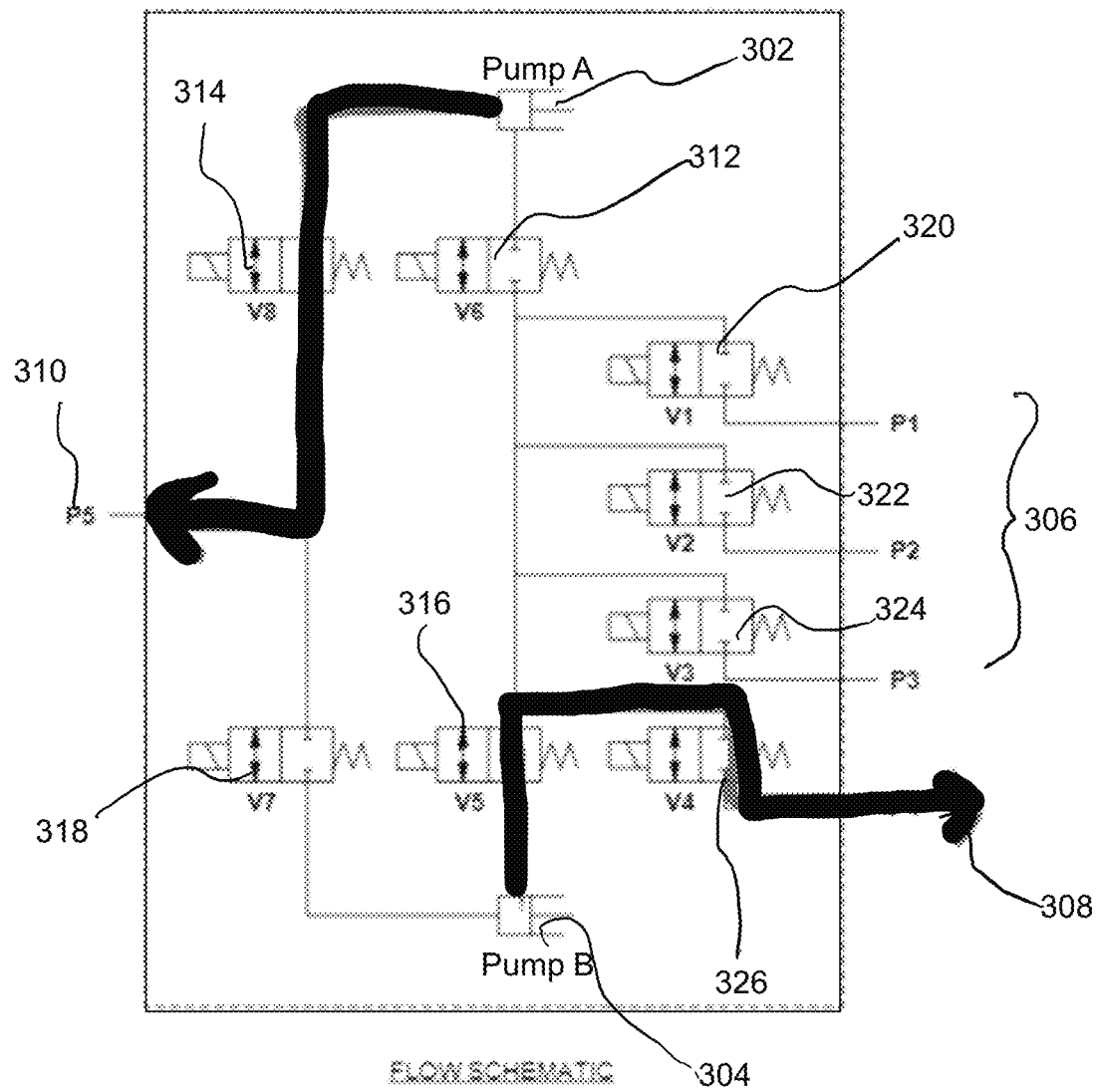
Figure 12:
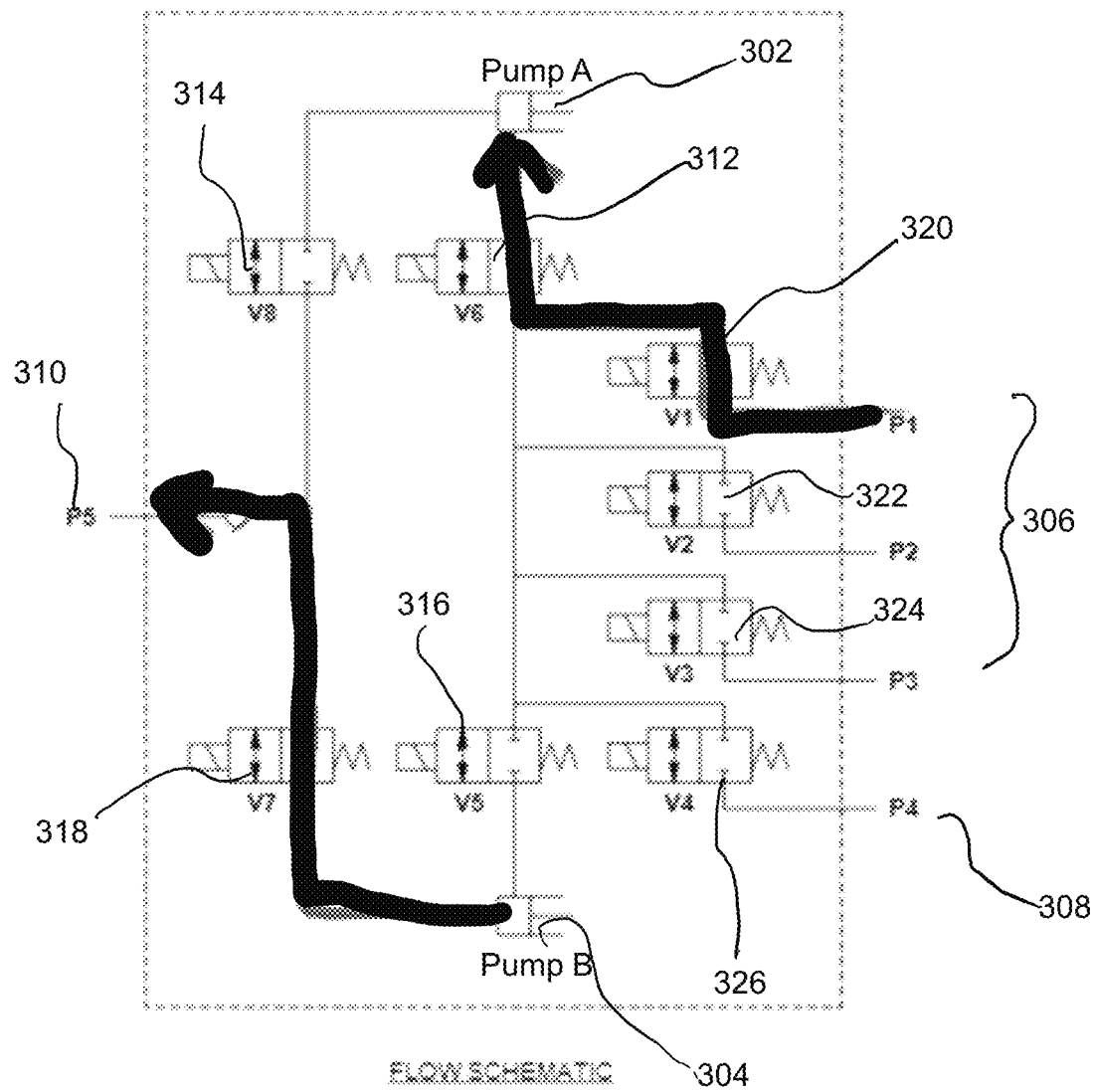

FIG. 8 shows initial operation in which pump A 302 may be initially filled or primed. For example, at the onset of the operation, both pumps may initial be empty. In this regard, a source port 306 may be connected to pump A 302 through valve 320 and valve 312 being opened to fill pump A 302. FIG. 9 shows that while pump A 302 ramps to speed, fluid communication between pump A 302 and waste port 308 may be established through valve 312 and valve 326. This may allow pump A 302 to come to equalization and speed while pumping to the waste port 308 rather than to the output port 310. During this time depicted in FIG. 9, pump B 304 may be idle. Once pump A 302 comes to steady-state operation, pump A 302 may be used to output fluid to output port 310 as depicted in FIG. 10 that shows pump A 302 is outputting to output port 310 through valve 314. While pump A 302 is providing fluid to the output port 310, pump B 304 may be filled from a source port 306 through valve 320 and valve 316. Prior to the exhaustion of the volumetric capacity of pump A 302, pump B 304 may ramp to speed while pumping to waste port 308 through valve 316 and valve 326 as shown in FIG. 11 that shows pump A 304 still outputting to output port 310 while Pump B 304 ramps to speed. In turn, pump A 302 may be isolated from the output port 310 by closure of valve 314 substantially simultaneously as pump B 304 being fluidly connected to output port 310 through valve 318 to maintain constant fluid flow to the output port 310 as pump B 304 may have attained operating speed prior to the change. In turn, pump B 304 may be used to supply fluid to output port 310 through valve 318 as shown in FIG. 12. In addition, pump A 302 may be filled or primed from a fluid source 306 while pump B 304 supplies fluid to the output port 310. While not shown, pump A 302 may thereafter initiate pumping to the waste port 308 to attain operational speed, and once attained, pump A 302 may thereafter be connected to output port 310 to supply fluid to the SPR system.

Accordingly, FIG. 13 shows an example of a state diagram 300 of the two displacement pumps 302 and 304 with respect to speed. As may be appreciated, the interleaving of operation of the pumps 302 and 304 may provide a constant flow rate to the output port 310 by filling and ramping up to speed of each pump while the other pump provides fluid to the output port 310. Further, FIG. 14 shows a flow diagram of an example of a pump procedure 350.

In another embodiment of the SPR system, instrument, and/or device, the dual pump system can also be used to virtually disconnect the pump from the flow cell without needing a ramp up time upon reconnection. This could be used to reduce pressure build up in the instrument when other valves like the injection valve or selector valve are actuated. Just before actuation, the pump flow can be diverted to the waste, the valve switched, and the flow diverted back to the flow cell, so that the pressure build up is minimized during switching of valves that are downstream from the pumps.

Figure 19:
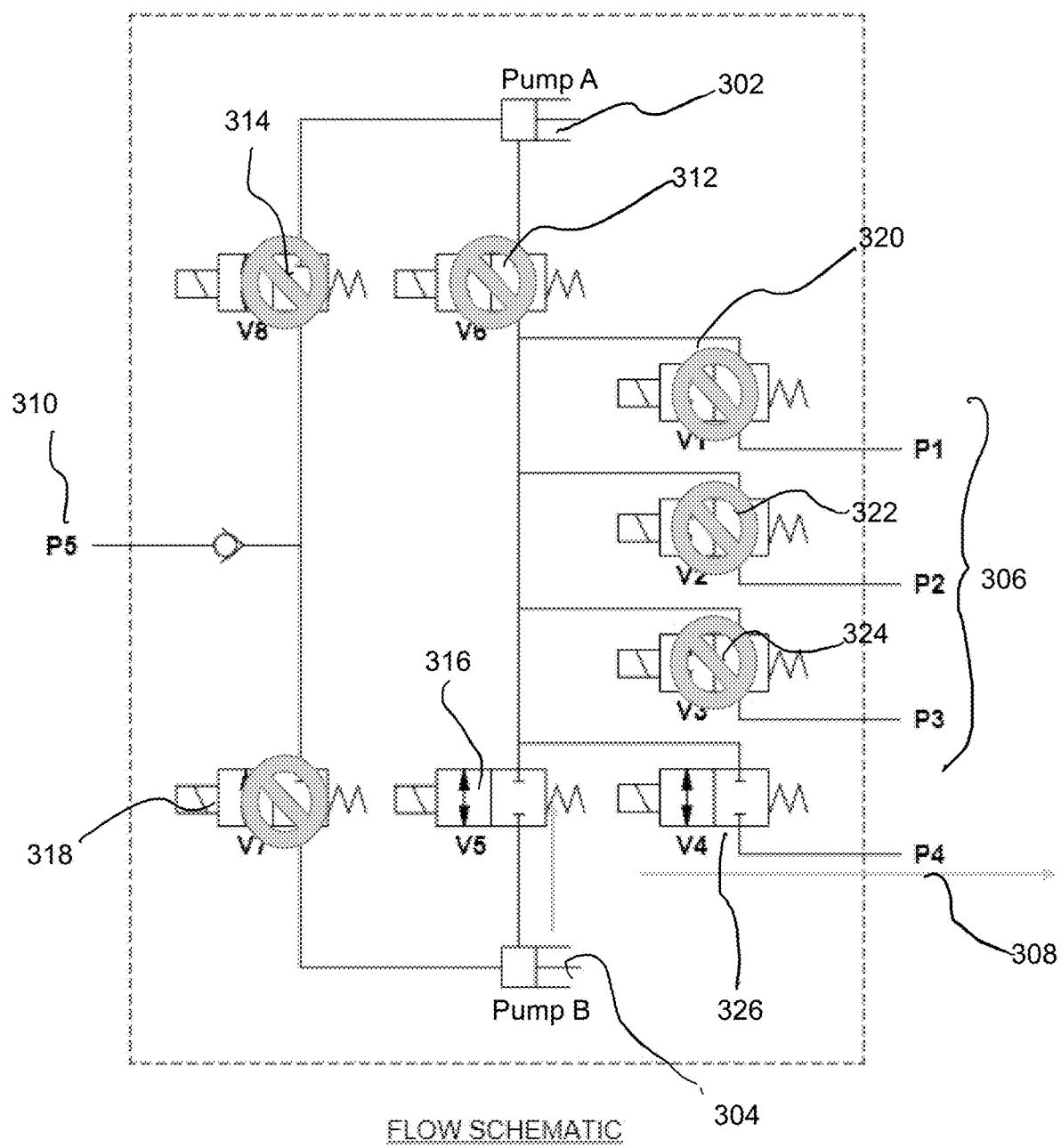
Figure 20:
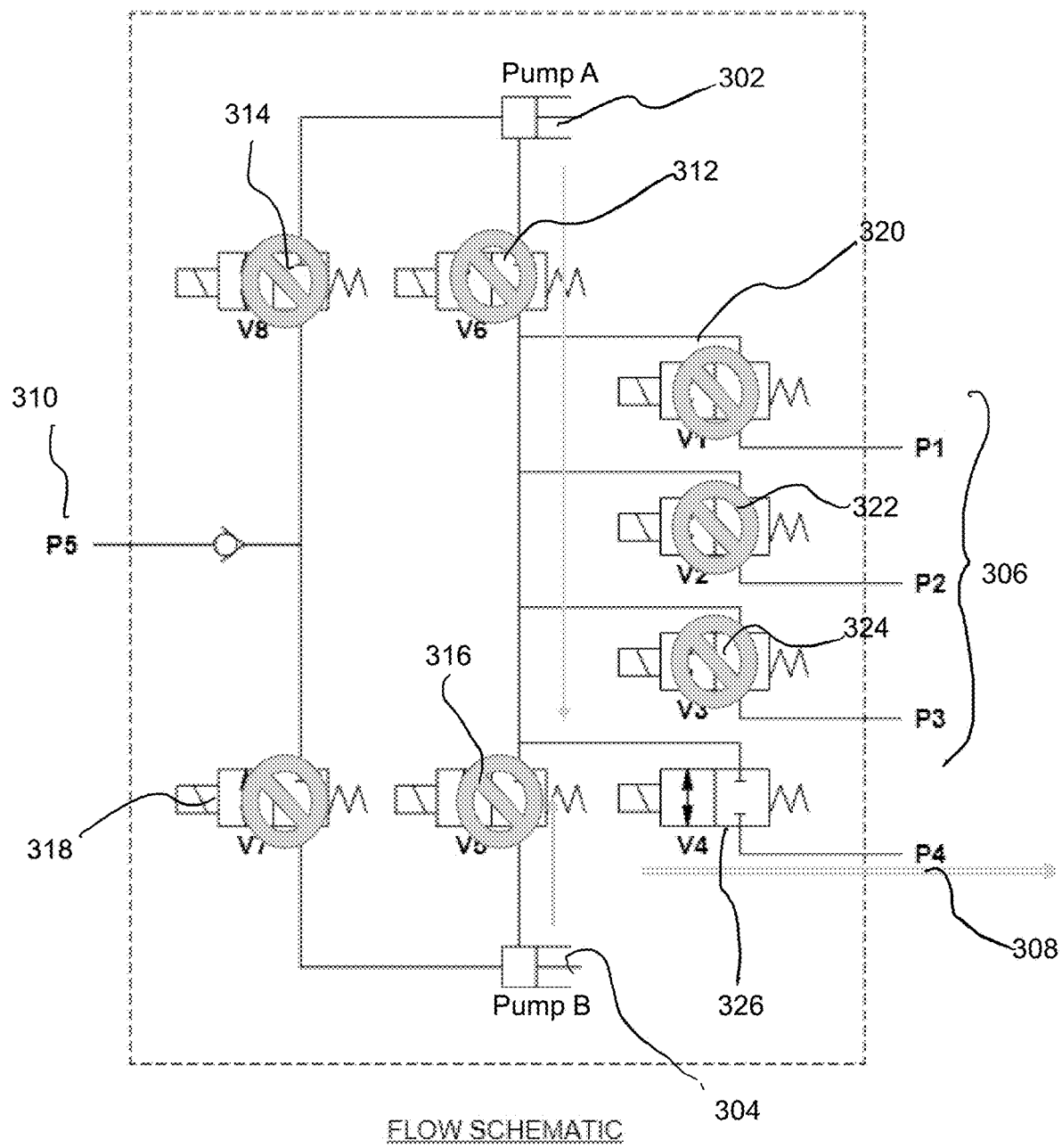
Figure 21:
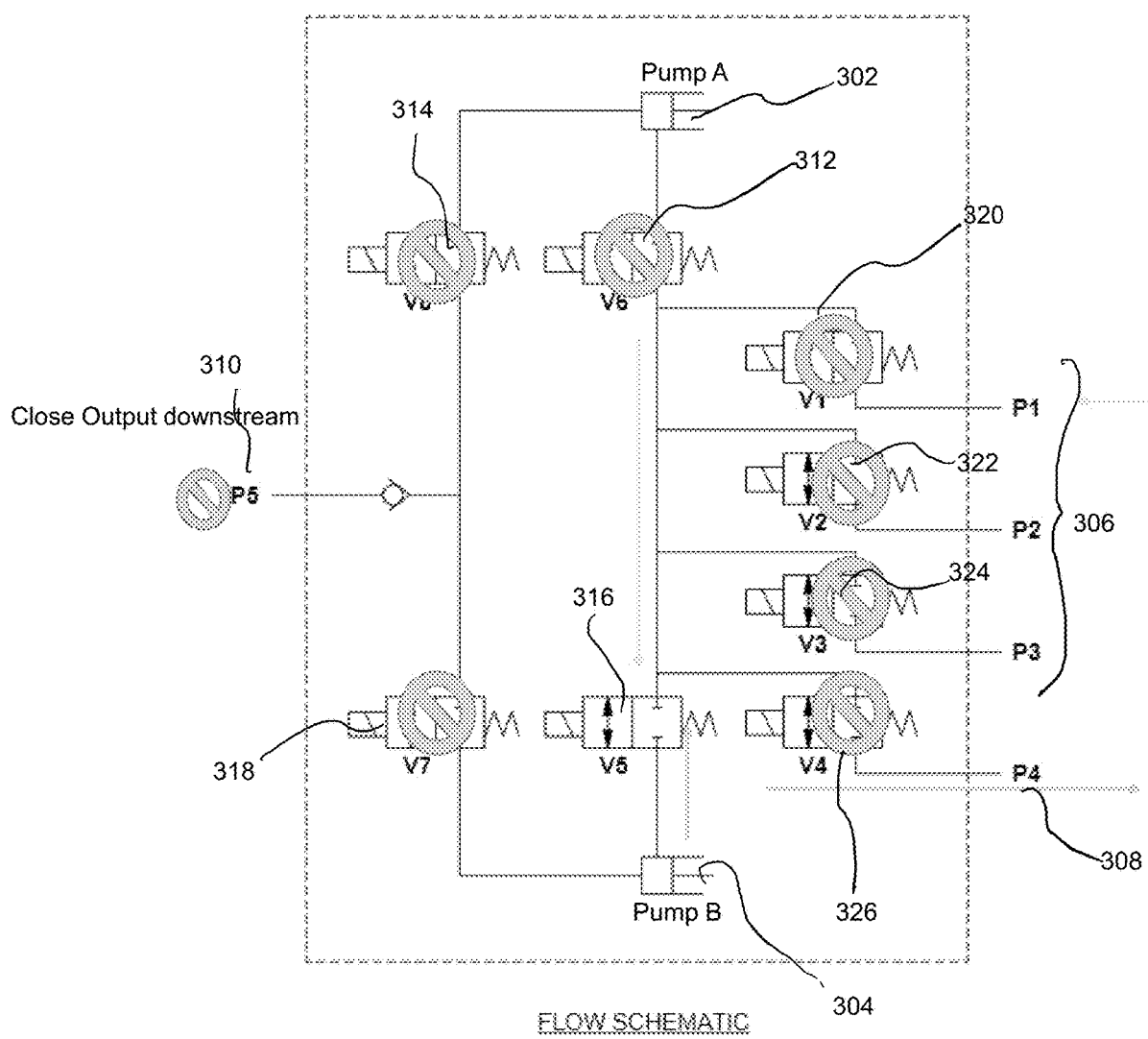
Figure 22:
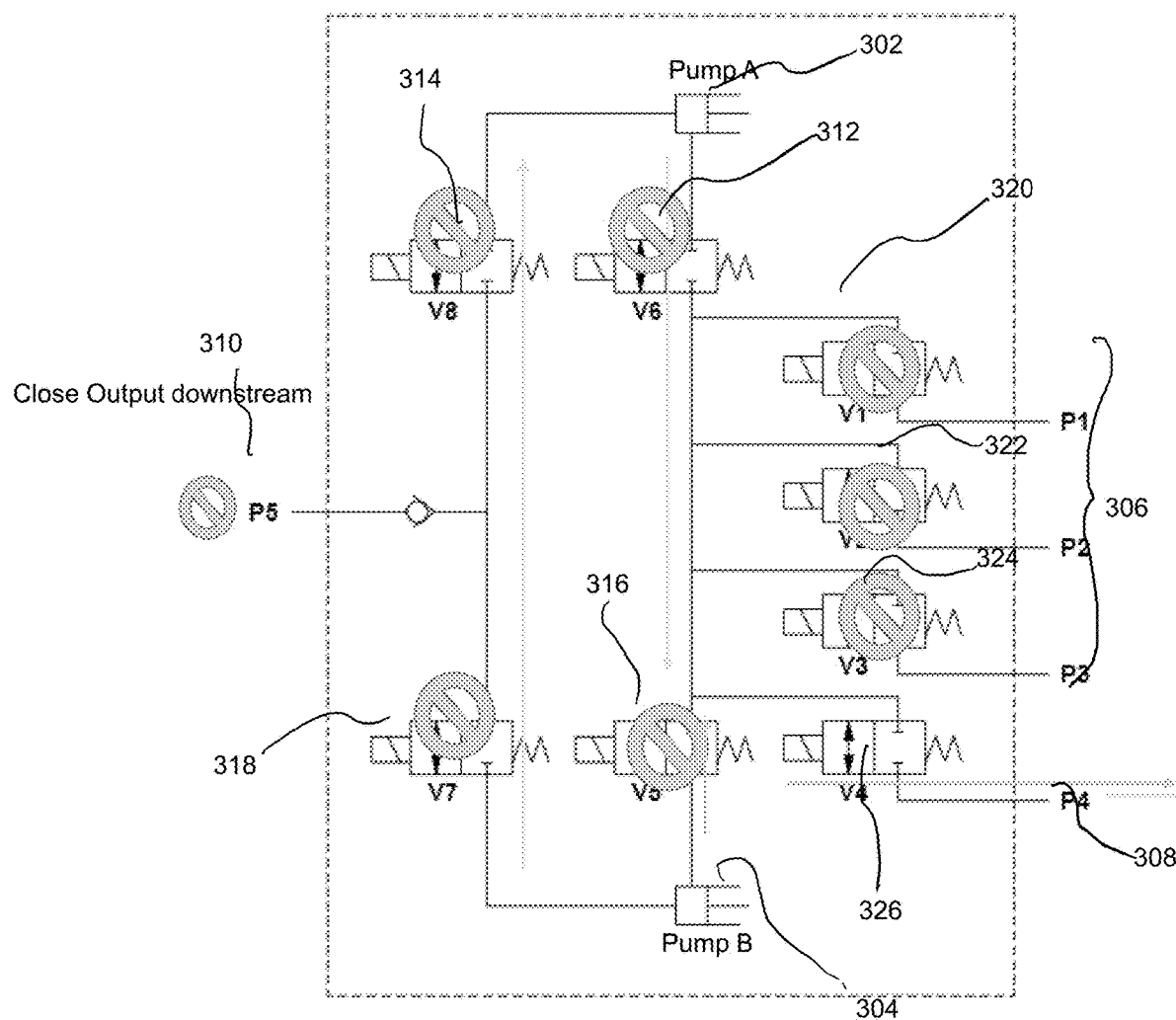

In yet another example, different buffers may have to be used in the SPR system. In turn, the buffers may be exchanged throughout the instrument, including the pumps. One way to accomplish such exchange may be to follow the embodiment of the buffer exchange sequence detailed in FIGS. 19, 20, 21, and 22. In this context, both pump A 302 and pump B 304 are to be connected to the new buffer. Accordingly, as shown in FIG. 19, pump B 304 may be purged to the waste port 308 and then pump A 302 may be purged to the waste port 308 as shown in FIG. 20. In turn, as shown in FIG. 21 pump B 304 may then be filled with the new buffer from a supply port 306, and the outlet port 310 may be closed by the intervening valves. Pump B 304 may then be purged to the waste port 308 through the longest possible route within the pump system, which in FIG. 22 is through valve 318, valve 314, pump A 302, valve 312, and valve 326 to waste port 308. This can be repeated multiple times from each pump as necessary to completely exchange the buffer.

In yet another embodiment of the SPR system, instrument, and/or device, the system can be used to reduce dispersion of samples injected into the flow cell. Dispersion may occur when the sample injected is in contact with the carrier buffer and a concentration gradient of the sample is created. As a result, the sample may disperse into the carrier buffer at the interface between the sample and the buffer. The amount of dispersion that occurs may be a function of time, with increased dispersion occurring as more time passes. It may be preferential to minimize the dispersion to have accurate kinetic measurements for SPR. As dispersion occurs over time, it may be important to minimize the amount of time it takes for the sample to go from the injection site to the SPR sensor (in the flow cell). One way to reduce the time in which dispersion may occur may be by having a first of the pumps in the dual pump system set at an "analysis flow rate" (AFR) and a second pump in the system set at a "transit flow rate" (TFR). The AFR may be the flow rate at which the kinetic assay is to be performed, typically 10-50 µl/min. The TFR may be a higher flow rate, such as, for example, 200 µl/min. Prior to (e.g., immediately prior to) the injection valve being switched to inject the sample, the TFR pump may be activated. The injection valve may be switched, and the sample maybe be rapidly transported to the SPR sensor spot due to the high speed of the TFR. Prior to (e.g. immediately prior to) the sample reaching the SPR sensor spot, the AFR pump may be activated, so that the SPR analysis can be performed at the appropriate analysis flow rate. In this way, the dispersion of the sample may be reduced. The reduction may be by a factor of TFR/AFR. For example, if AFR=10 and TFR=200, the dispersion would be reduced by a factor of ~20. The above method can also be used with a single pump to reduce dispersion but may involve additional time in between flow rate changes to allow the rate to stabilize before analysis.

In another example, the SPR instrument may be connected to additional fluid handling systems, such as for automation, which may impart additional volume between the flow cell and sample, which would increase dispersion. To reduce dispersion, a two injection valve system can be used, in which the other fluid handling system may inject a sample into the injection valve of the SPR system. The sample can be transported at the TFR to reduce dispersion, or small air gaps can be used at the start and end of the sample to also reduce dispersion.

Another embodiment of a PR system, instrument, and/or device including a dual channel LSPR sensor may also be provided. Making an LSPR using a top down process instead of a bottom up process means there may be more variability in the manufacturing process and hence more variability in the sensor properties. By contrast, the dual channel LSPR sensor of this embodiment may provide highly consistent sensor properties (e.g., sensitivity, noise, decay length). By making a single sensor spot that is large enough to be covered by two fluidic channels and interrogated by two different spectral detectors, the variability in the sensor properties between the channels can be reduced.

By way of example, FIG. 15, FIG. 16, and FIG. 17 show a front view, a back view, and an exploded view, respectively, of an embodiment of a flow cell 400 that includes a dual channel LSPR sensor. Such a flow cell 400 may be provided in an embodiment in lieu of the flow cell 160 shown in FIGS. 1-5. The flow cell 400 may include three ports (e.g., port A, port B, and a waste port), a U-shaped channel with a 6 port valve (not shown), and 3 port selector valve (not shown). In turn, two channels (e.g., channel 1 and channel 2) may be provided that may each be fluidly coupled to the U-shaped channel. Accordingly, channel 2 may be addressed individually, or the channels can be addressed collectively (e.g., channel 1 and channel 2). This may allow two different ligands to be functionalized on each channel or may allow for blocking one channel to use as a reference channel and the other as the active channel with a ligand. This is not limited to only two channels as the same design can be replicated a plurality of times over the sensor spot to create more than two detection sites.

In one example and referring still to FIG. 15, FIG. 16, and FIG. 17, the process flow for a carboxyl sensor chip that may be configured for one reference channel and one active sensing channel may include the following steps.
1) Inject EDC/NHS through channel 1+channel 2 (e.g., activate port A)
2) Switch selector valve to select only port B (e.g., for flow in channel 2 only)
3) Inject ligand through channel 2
4) Switch selector valve to select port A (e.g. to provide flow in channel 1 and channel 2)
5) Inject blocking solution through channel 1 and channel 2 (e.g. maintaining selection to port A)
6) Inject analytes through channel 1 and channel 2 (e.g. maintaining selection the port A) to perform kinetic or affinity assay In another example and referring still to FIG. 15, FIG. 16, and FIG. 17, the process flow for a carboxyl sensor chip that may be configured for two sensor channels with a different ligand on each channel may include the following steps.
1) Inject EDC/NHS through channel 1+channel 2 (i.e., activate port A)
2) Switch selector valve to select only port B (e.g., for flow in channel 2 only)
3) Inject ligand 1 through channel 2 while maintaining selection of port B
4) Inject blocking solution through channel 2 while maintaining selection of port B
5) Switch selector valve to port A (for flow through channel 1 and channel 2)
6) Inject ligand 2 through channel 1+channel 2 while maintaining selection of port A
7) Inject blocking solution through channel 1 and channel 2 while maintaining selection of port A
8) Inject analytes through channel 1 and channel 2 while maintaining selection of port A to perform kinetic or affinity assay on ligand 1 and ligand 2 simultaneously For one reference channel and one active sensing channel, the reference channel can be used to subtract out drift, bulk refractive index changes, and non-specific binding by subtracting the reference channel from the sensor channel. An example of results from this two-channel instrument for protein interaction analysis are shown in FIG. 18A and FIG. 18B.

In another example, two completely independent linear channels each with its own inlet and outlet could be used to implement two channels. Each channel may travel over different areas of the same sensor spot. A T-junction can be used with selector and injection valves to split the flow going to the two channels when needed, such as when a common analyte solution is to be passed through each channel. This embodiment may include any aspect described in Provisional Application No. 62/715,137, the entirety of which is incorporated by reference herein.

In another example, a different nanostructure can be used in each channel with the same ligand on both channels, so binding data can be acquired from two different sets of sensitivity and decay length, providing a nanoscale ellipsometer. This may enable solving for thickness and RI of the layers, essentially providing both binding data and conformation change data.

In another example, two different nanoparticles can be located within each channel, so that within each channel bulk RI or non-specific binding controls can be done, effectively providing four channels. Each channel can be functionalized with a different ligand or can use one as a reference but could also acquire the binding and conformation data from each channel.

In another example, an LED may be provided on a board 130 (e.g., PCB) that may be easily interchangeable so that different light sources can be installed by the user. The board 130 may include a plug-in socket style connect and a fastener for quickly and efficiently interchanging the board 130 with alternative boards 130 with different light sources. Also, there could be multiple LEDs on a single board that may be selectively activated or activated in conjunction.

In another example, on the same LED board 130 there could be a UV LED that may be positioned to illuminate through the side the of the flow cell, allowing fluorescent measurements to be simultaneously or independently performed on the same SPR system. In another example of a fluorescent measurement, optical filters could be installed both between the LED or UV LED and the sensing spot and the spectrometer.

In another example, the flow cell 106 may include a rigid portion and soft portion that are bonded together to form a fluidic seal. The rigid portion may be made of a hard polymer like PMMA or cyclic olefin copolymer and the soft portion may be made from a soft polymer like PDMS or Viton that can provide a seal against a glass or plastic surface. The LED may be located directly behind the rigid piece in line with the SPR sensor on the sensor chip 104. A waveguide or light pipe may be cut into the rigid part of the flow cell 106 by cutting out the outline of a cylinder in the rigid portion and leaving the resulting void filled with air. This may effectively increase the light throughput to the SPR sensor and subsequently detector, increasing performance.

In another example, the sensor chip holder 120 can be user swappable to a cuvette holder. This allows a cuvette to be placed inside the cuvette holder, and the same optical system used to measure the optical properties of the solution or substance inside the cuvette. The two optical channels can be used to either provide dual measurements of the same cuvette, or measurements from two independent cuvette channels simultaneously in the holder. Temperature control of the cuvette can be implemented with either of the two previous designs disclosed.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the appended claims.

What is claimed is:

1. A plasmon resonance system for measuring properties of molecular interactions, comprising:
    a sensor chip comprising a detection region;
    a flow cell comprising a fluid channel for circulating a fluid across said detection region of said sensor chip;
    an actuator configured to control relative movement of said sensor chip with respect to said flow cell between an undocked configuration in which said sensor chip is spaced apart from said flow cell and a docked configuration in which said sensor chip is in contact with said flow cell to seal a volume of space between said sensor chip and said flow cell;
    a load sensor configured to determine a force between said sensor chip and said flow cell resulting from movement of said actuator; and
    a controller configured to receive a signal from said load sensor, said signal indicative of a magnitude of said force, and to cease movement of said actuator in response to said magnitude exceeding a threshold value, wherein said threshold value corresponds to a force associated with said docked configuration.

2. The plasmon resonance system of claim 1, wherein said actuator is an electrically-driven linear actuator.

3. The plasmon resonance system of claim 1, further comprising:
    a shuttle supporting one of said sensor chip and said flow cell, said shuttle in operative engagement with said actuator for linear movement of said one of said sensor chip and said flow cell with respect to the other one of said sensor chip and said flow cell; and
    a pedestal supporting said other one of said sensor chip and said flow cell.

4. The plasmon resonance system of claim 1, wherein said sensor chip comprises either glass or plastic and said flow cell comprises either polydimethylsiloxane or a fluoroelastomer.

5. The plasmon resonance system of claim 1, further comprising:
    an optical system configured to determine a displacement, of a portion of said flow cell occurring in response to a force between said sensor chip and said flow cell resulting from movement of said actuator.

6. The plasmon resonance system of claim 5, wherein said portion of said flow cell is an elastically deformable channel configured to collapse in response to a collapse force from said actuator.

7. The plasmon resonance system of claim 6, wherein said elastically deformable channel is a portion of said fluid channel.

8. The plasmon resonance system of claim 7, wherein said actuator is configured to retract a preset distance in response to said optical system determining said elastically deformable channel has collapsed.

9. The plasmon resonance system of claim 7, wherein said optical system comprises a photodiode.

10. The plasmon resonance system of claim 7, wherein said optical system comprises a white light emitting diode on a side of said portion of said flow cell and a spectrometer on an opposing side of said portion of said flow cell, wherein said spectrometer is configured to detect a change in an optical property resulting from said collapse of said portion of said flow cell.

11. The plasmon resonance system of claim 10, wherein said optical property is one of absorbance spectra and refractive index.

12. The plasmon resonance system of claim 1, further comprising a thermal control device disposed in close proximity to said sensor chip, wherein said thermal control device is configured to modulate a temperature of said sensor chip.

13. The plasmon resonance system of claim 12, wherein said thermal control device comprises an aperture configured to allow light to pass therethrough.

14. The plasmon resonance system of claim 12, further comprising a thermocouple configured to measure a temperature of said thermal control device, wherein said thermocouple is electrically coupled to said controller.

15. The plasmon resonance system of claim 1, wherein said flow cell further comprises a first fluid channel extending between a first inlet port and an intersection with a second fluid channel, said second fluid channel extending between a second inlet port and an outlet port.

16. The plasmon resonance system of claim 15, further comprising a selector valve configured to select either said first inlet port or said second inlet port for injection of said fluid.

17. The plasmon resonance system of claim 16, wherein said intersection is y-shaped and configured to prevent said fluid injected through said second inlet port from passing into said first fluid channel.

18. The plasmon resonance system of claim 6, wherein said portion of said flow cell comprises a plurality of measurement indentations, each configured to collapse under a different predetermined magnitude of force, such that said plasmon resonance system may determine a magnitude of said force between said sensor chip and said flow cell based on which of said plurality of measurement indentations are collapsed as determined by said optical system.

* * * * *